US008986656B2

(12) United States Patent
Yamada et al.

(10) Patent No.: US 8,986,656 B2
(45) Date of Patent: Mar. 24, 2015

(54) METHOD FOR EVALUATING SPECIFIC INCORPORATION OF D-GLUCOSE INTO CELLS

(75) Inventors: Katsuya Yamada, Aomori (JP); Hideaki Matsuoka, Tokyo (JP); Tadashi Teshima, Osaka (JP); Toshihiro Yamamoto, Osaka (JP)

(73) Assignees: Hirosaki University, Hirosaki-Shi (JP); National University Corporation Tokyo Unversity of Agriculture and Technology, Tokyo (JP)

( * ) Notice: Subject to any disclaimer, the term of this patent is extended or adjusted under 35 U.S.C. 154(b) by 368 days.

(21) Appl. No.: 13/058,061

(22) PCT Filed: Aug. 7, 2009

(86) PCT No.: PCT/JP2009/064053
§ 371 (c)(1),
(2), (4) Date: Apr. 20, 2011

(87) PCT Pub. No.: WO2010/016587
PCT Pub. Date: Feb. 11, 2010

(65) Prior Publication Data
US 2011/0189708 A1 Aug. 4, 2011

(30) Foreign Application Priority Data

Aug. 8, 2008 (JP) ................................. 2008-205708

(51) Int. Cl.
*G01N 33/58* (2006.01)
*G01N 33/50* (2006.01)
*C12Q 1/54* (2006.01)
*C12Q 1/02* (2006.01)
*G01N 33/533* (2006.01)

(52) U.S. Cl.
CPC .. *C12Q 1/54* (2013.01); *C12Q 1/02* (2013.01); *G01N 33/5005* (2013.01); *G01N 33/533* (2013.01); *G01N 33/582* (2013.01)
USPC ........................................................ 424/9.6

(58) Field of Classification Search
CPC .......... C12Q 1/02; C12Q 1/54; G01N 33/582; G01N 33/533; G01N 33/5005
See application file for complete search history.

(56) References Cited

U.S. PATENT DOCUMENTS 6,207,136 B1 3/2001 Matsuoka
6,989,140 B2* 1/2006 Tidmarsh et al. ............... 424/9.1
2009/0317829 A1 12/2009 Thorson et al.

FOREIGN PATENT DOCUMENTS

JP 2958447 7/1999

OTHER PUBLICATIONS

Ermolenko "Asymmetric synthesis of amino sugars. Part 2. A novel versatile approach to the chiral non-racemic synthesis of 2-amino-2-deoxy sugars. Preparation of L-glucosamine, L-mannosamine and L-talosamine derivatives" Journal of the Chemical Society Perkins Transactions 1, 2000, 2465-2473.*
Germinario "Kinetic Characteristics and Regulation of Hexose Transport in a Galactokinse-Negative Chinese Hamster Fibroblast Cell Line: A Good Model for Studies on sugar Transport in Cultured Mammalian Cells" Journal of Cellular Physiology 1989, 138: 300-304.*
Carter "Glucose Transport in Plasma Membrane Vesicles from Rat Adipose Tissue" Journal of Biological Chemistry, 1972, vol. 247, No. 9, 2682-2688.*
Achilles ("Affinity of Single *S. cerevisiae* cells to 2-NBDGGLucose Under Changing Substrate Concentrations" Cytometry Part A, 61A, (2004), 88-98.*
K. Yamada, et al.; "A real-time method of imaging glucose uptake in single, living mammalian cells;" Nature Protocols; vol. 2; No. 3; 2007; pp. 753-762 and end sheet (11 Sheets).
K. Yamada, et al.; "Application of highly pure fluorescent glucose derivative 2-NBDG into neurons;" Neuroscience Research; vol. 61; Suppl. 1; Jul. 2008; p. S138(P1-v14) and title page (2 Sheets).
C. Conde, et al.; "An Hg-sensitive channel mediates the diffusional component of glucose transport in olive cells;" Biochimica Biophysica Acta; vol. 1768; No. 11; 2007; pp. 2801-2811 (11 Sheets).
J. Levi, et al.; "Fluorescent Fructose Derivatives for Imaging Breast Cancer Cells;" Bioconjugate Chem.; vol. 18; No. 3; 2007; pp. 628-634 (7 Sheets).
L. Speizer, et al.; "Asymmetric transport of a fluorescent glucose analogue by human erythrocytes;" Biochemica Biophysica Acta; vol. 815; No. 1; 1985; pp. 75-84 (10 Sheets).

(Continued)

*Primary Examiner* — Jon P Weber
*Assistant Examiner* — Charles Zoltan Constantine
(74) *Attorney, Agent, or Firm* — Kratz, Quintos & Hanson, LLP

(57) ABSTRACT

An object of the present invention is to provide a method for accurately evaluating the specific incorporation of D-glucose into cells. The present invention as a means for achieving the object is characterized by comprising contacting a D-glucose derivative that has a fluorescent chromophore in the molecule and is specifically incorporated into cells and an L-glucose derivative that has a fluorescent chromophore in the molecule with different cells in the same cell strain to be evaluated, respectively, comparing the fluorescence emitted by the D-glucose derivative that has a fluorescent chromophore in the molecule and is specifically incorporated into cells with the fluorescence emitted by the L-glucose derivative that has a fluorescent chromophore in the molecule, and evaluating the specific incorporation of D-glucose into cells relative to L-glucose by taking the difference between the two kinds of fluorescence intensities.

12 Claims, 4 Drawing Sheets
(1 of 4 Drawing Sheet(s) Filed in Color)

(56) References Cited

OTHER PUBLICATIONS

J. Halama, et al.; "Validation of 3-deoxy-3 fluoro-D-glucose as a glucose transport analogue in rat heart;" Am. J. Physiol.; vol. 247; No. 5; Pt. 2; 1984; p. H754-H759 (6 Sheets).

T. Yamamoto, et al.; "Synthesis of 2-NBDLG, a fluorescent derivative of L-glucosamine; the anitpode of D-glucose tracer 2-NBDG;" Tetrahedron Letters; vol. 49; No. 48; Nov. 24, 2008; pp. 6876-6878 (3 Sheets).

International Search Report for International Application No. PCT/JP2009/064053 dated Oct. 13, 2009.

Yamada, K. et al., "Imaging Sterospecific Uptake of Glucose Using Fluorescent D-and L-Glucose Analogues", *Journal of Physiological Sciences*, vol. 59, No. Suppl. 1, 2009, p. 152, XP002649274.

Database BIOSIS [Online], *Biosciences Information Service*, Philadelphia, PA, US, Mar. 7, 2001, Kloda, D. G. et al., "Glucose toxicity induces myocardial insulin resistance", XP002649275.

Germinario,R.J. et al., "Saturable and Nonsaturable Hexose Uptake in Cultured Human Skin Fibroblasts", *Canadian Journal of Biochemistry*, vol. 56, No. 2, 1978, pp. 80-88, XP009150122.

Carter, J. R. et al., "Glucose transport by trypsin-treated red blood cell ghosts", *Biochimica Et Biophysica Acta. Biomembranes, Amsterdam, NL*, vol. 291, No. 2, Jan. 26, 1973, pp. 506-518, XP025416460.

Ludvigsen, C. et al., "A Kinetic Analysis of D Glucose Transport by Adipocyte Plasma Membranes", *Journal of Biological Chemistry*, vol. 254, No. 5, 1979, pp. 1444-1446, XP002649276.

Extended Supplementary European Search Report dated Sep. 9, 2011, in counterpart European Application No. 09805069.3.

Johnston, Thomas P., et al., "L-Chlorozotocin," Journal of Medicinal Chemistry (1979), vol. 22, No. 5, pp. 597-599.

Yoshioka, Kazuaki, et al., "A novel fluorescent derivative of glucose applicable to the assessment of glucose uptake activity of *Escherichia coli*," Biochimica et Biophysica Acta 1289 (1996), pp. 5-9.

Yamada, Katsuya, et al.; "Application of highly pure fluorescent glucose derivative 2-NBDG into neurons," poster presented at the 31st Annual Meeting of the Japan Neuroscience Society, Jul. 2008.

Cura, AJ. & Carruthers, A., "Role of Monosaccharide Transport Proteins in Carbohydrate Assimilation, Distribution, Metabolism, and Homeostasis," Compr. Physiol. 2: 863-914 (2012).

Zhao F.-Q, and Keating, AF, "Functional Properties and Genomics of Glucose Transporters," Current Genomics 8:113-128 (2007).

Barrett, MP, et al., "Structure and function of facilitative sugar transporters," Current Opinion in Cell Biology 11:496-502 (1999).

Thorens, B. & Mueckler, M., "Glucose transporters in the 21st Century," Am. J. Physiol. Endocrinol. Metab. 298:E141-E145 (2010).

Vera, JC. et al., "Mammalian facilitative hexose transporters mediate the transport of dehydroascorbic acid," Nature 364; 79-82 (1993).

Duran C. et al., "Chloride Channels: Often enigmatic, rarely predictable," Ann. Rev. Physiol. 72: 95-121 (2010).

Loaiza, A. et al., "Glutamate Triggers Rapid Glucose Transport Stimulation in Astrocytes as Evidenced by Real-Time Confocal Microscopy," J. Neurosci. 23: 7337-7342 (2003).

Lloyd, PG, et al., "Examining Glucose Transport in Single Vascular Smooth Muscle Cells with a Fluorescent Glucose Analog," Physiol. Res. 48: 401-410 (1999).

Cheng, Z., et al., "Near-infrared Fluorescent Deoxyglucose Analog for Tumor Optical Imaging in Cell Culture and in Living Mice," Bioconjugate Chem. 17: 662-669 (2006).

Sokoloff L., et al., "The [14C] Deoxyglucose Method for the Measurement of Local Cerebral Glucose Utilization: Theory, Procedure, and Normal Values in the Conscious and Anesthetized Albino Rat," J. Neurochem, 28: 897-916 (1977).

Levi, J., et al., "Fluorescent Fructose Derivatives for Imaging Breast Cancer Cells," Bioconjug. Chem. 18:628-634 (2007).

Blasco, T., et al., "Expression and Molecular Characterization of Rat Renal D-Mannose Transport in Xenopus Oocytes," Membrane Biol. 178, 127-135 (2000).

Mendelssohn, D.C. & Silverman, M., "A D-mannose transcript system in renal brush-border membranes," Am. J. Physiol. 257: F110-1107 (1989).

Nimmerjahn, A, et al., "Sulforhodamine 101 as a specific marker of astroglia in the neocortex in vivo," Nature Methods 1: 1-7 (2004).

\* cited by examiner

Incorporation of 2-NBDG or 2-NBDLG into live cells of Escherichia coli K12

(50 μM for 10 min at 37°C)

Combination and wavelength separation of fluorescent glucose derivatives that emit fluorescence at three different wavelengths

METHOD FOR EVALUATING SPECIFIC INCORPORATION OF D-GLUCOSE INTO CELLS

TECHNICAL FIELD

The present invention relates to a method for accurately evaluating the specific incorporation of D-glucose into cells.

BACKGROUND ART

Glucose is known as one of the most important energy sources for maintaining the survival of cells, from mammals to *Escherichia coli* and yeast, and in particular, the brain uses glucose as the sole energy source. Glucose has enantiomers D-glucose and L-glucose, and among these enantiomers, only D-glucose can be utilized as an energy source by organisms, and living cells have a mechanism of selectively incorporating D-glucose mediated by a transport protein in the cell membrane such as a glucose transporter and utilizing it.

In the past, a research as to how organisms incorporate D-glucose into cells and utilize it has been performed by determining the amount of a radioisotope in cells using, for example, radiolabelled D-glucose or a derivative thereof (such as radiolabelled D-deoxyglucose). However, although this method is excellent in quantitative determination, it has a problem that the sensitivity is low, and also has a disadvantage from a measurement method point of view that it cannot continuously observe the manner that living cells incorporate D-glucose in real time. Therefore, this method cannot be used in a study of the process of dynamic incorporation of D-glucose into living cells.

In view of the above circumstances, the group of the present inventors proposed a method using 2-[N-(7-nitrobenz-2-oxa-1,3-diazol-4-yl)amino]-2-deoxy-D-glucose (2-NBDG) that is represented by the following structural formula and emits green fluorescence and is obtained by attaching an N-(7-nitrobenz-2-oxa-1,3-diazol-4-yl)amino group as a fluorescent chromophore to the 2-position of D-deoxyglucose as the method which can be used in a study of the process of dynamic incorporation of D-glucose into living cells, and the usefulness of the method was demonstrated using various mammalian cells (Non-patent document 1).

[Chemical 1]

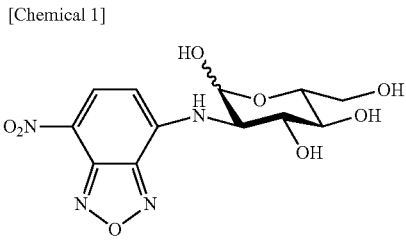

2-NBDG

This method utilizes the property of 2-NBDG that it is selectively incorporated into living cells, and by tracking changes in the fluorescence intensity due to the incorporation, the dynamic activity of cells for the incorporation of D-glucose can be quantitatively determined. Therefore, this method has been evaluated by researchers around the world as an innovative method in studies as to how organisms incorporate D-glucose into cells and utilize it, and now is positioned as a standard protocol essential in this research field (Non-patent document 2).

PRIOR ART DOCUMENTS

Non-Patent Documents

Non-patent document 1: Yamada K. et al., J. Biol. Chem. 275: 22278-22283, 2000
Non-patent document 2: Yamada K. et al., Nat. Protoc. 2: 753-762, 2007

SUMMARY OF THE INVENTION

Problems that the Invention is to Solve

In Non-patent document 1, the group of the present inventors administered 2-NBDG to insulin-secreting cells which are representative cells expressing GLUT2 that is a low-affinity (high-Km) glucose transporter, and revealed, from changes in the fluorescence intensity, that 2-NBDG is incorporated into cells depending on the concentration, time, and temperature, and the Km value thereof is equivalent to the value reported for D-glucose. Therefore, it can be said that according to this method, the incorporation of D-glucose mediated by GLUT2 that is a high-Km glucose transporter can be quantitatively evaluated. However, in the case where there is 2-NBDG nonspecifically or specifically adsorbed onto the surface of the cell membrane or in the membrane, 2-NBDG nonspecifically incorporated into cells without being mediated by the glucose transporter, or the like, the fluorescence intensity obtained by the administration of 2-NBDG includes the fluorescence emitted by such 2-NBDG.

Therefore, in order to accurately evaluate the specific incorporation of D-glucose into cells, it is necessary to consider the existence of such 2-NBDG, and this is considered to be very important when the kinetics of the incorporation of 2-NBDG mediated by GLUT1 that is a high-affinity (low-Km) glucose transporter expressed in many cells, GLUT3 expressed in neurons, or the like is studied. However, there has been no report as to how this point is reflected in the experimental method.

In view of this, an object of the present invention is to provide a method for accurately evaluate the specific incorporation of D-glucose into cells.

Means for Solving the Problems

As a result of intensive studies in view of the above circumstances, the present inventors conceived an idea that when a difference in the fluorescence intensity between before and after administration of 2-NBDG to cells to be evaluated is measured, a fluorescent L-glucose derivative which is not specifically incorporated into cells is used as a control.

A method for evaluating the specific incorporation of D-glucose into cells relative to L-glucose according to the present invention based on the above idea is characterized by comprising contacting a D-glucose derivative that has a fluorescent chromophore in the molecule and is specifically incorporated into cells and an L-glucose derivative that has a fluorescent chromophore in the molecule with different cells in the same cell strain to be evaluated, respectively, comparing the fluorescence emitted by the D-glucose derivative that has a fluorescent chromophore in the molecule and is specifically incorporated into cells with the fluorescence emitted by the L-glucose derivative that has a fluorescent chromophore in the molecule, and evaluating the specific incorporation of D-glucose into cells relative to L-glucose by taking the difference between the two kinds of fluorescence intensities as described in claim 1.

Further, the method described in claim 2 is characterized in that in the method described in claim 1, as the D-glucose derivative that has a fluorescent chromophore in the molecule and is specifically incorporated into cells, a D-glucose derivative that has an N-(7-nitrobenz-2-oxa-1,3-diazol-4-yl)amino group in the molecule is used.

Further, the method described in claim 3 is characterized in that in the method described in claim 2, as the D-glucose derivative that has an N-(7-nitrobenz-2-oxa-1,3-diazol-4-yl) amino group in the molecule, D-deoxyglucose having an N-(7-nitrobenz-2-oxa-1,3-diazol-4-yl)amino group attached to the 2-position thereof is used.

Further, the method described in claim 4 is characterized in that in the method described in claim 2, as the L-glucose derivative that has a fluorescent chromophore in the molecule, an L-glucose derivative that has an N-(7-nitrobenz-2-oxa-1,3-diazol-4-yl)amino group in the molecule is used.

Further, the method described in claim 5 is characterized in that in the method described in claim 4, as the L-glucose derivative that has an N-(7-nitrobenz-2-oxa-1,3-diazol-4-yl) amino group in the molecule, L-deoxyglucose having an N-(7-nitrobenz-2-oxa-1,3-diazol-4-yl)amino group attached to the 2-position thereof is used.

Further, the method described in claim 6 is characterized in that in the method described in claim 1, as the D-glucose derivative that has a fluorescent chromophore in the molecule and is specifically incorporated into cells, a D-glucose derivative that has a 2-(N-methylamino)benzoylamino group in the molecule is used.

Further, the method described in claim 7 is characterized in that in the method described in claim 6, as the D-glucose derivative that has a 2-(N-methylamino)benzoylamino group in the molecule, D-deoxyglucose having a 2-(N-methylamino)benzoylamino group attached to the 2-position thereof is used.

Further, the method described in claim 8 is characterized in that in the method described in claim 6, as the L-glucose derivative that has a fluorescent chromophore in the molecule, an L-glucose derivative that has a 2-(N-methylamino) benzoylamino group in the molecule is used.

Further, the method described in claim 9 is characterized in that in the method described in claim 8, as the L-glucose derivative that has a 2-(N-methylamino)benzoylamino group in the molecule, L-deoxyglucose having a 2-(N-methylamino)benzoylamino group attached to the 2-position thereof is used.

Further, the method for evaluating the specific incorporation of D-glucose into cells relative to L-glucose according to the present invention is characterized by comprising contacting a mixture of a D-glucose derivative that has a fluorescent chromophore in the molecule and is specifically incorporated into cells and an L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells with cells to be evaluated, and detecting the fluorescence emitted by the D-glucose derivative that has a fluorescent chromophore in the molecule and is specifically incorporated into cells as described in claim 10.

Further, the method described in claim 11 is characterized in that in the method described in claim 10, a difference in the maximum fluorescence wavelength is set to at least 20 nm.

Further, the method described in claim 12 is characterized in that in the method described in claim 10, as the D-glucose derivative that has a fluorescent chromophore in the molecule and is specifically incorporated into cells, a D-glucose derivative that has an N-(7-nitrobenz-2-oxa-1,3-diazol-4-yl)amino group in the molecule is used.

Further, the method described in claim 13 is characterized in that in the method described in claim 12, as the D-glucose derivative that has an N-(7-nitrobenz-2-oxa-1,3-diazol-4-yl) amino group in the molecule, D-deoxyglucose having an N-(7-nitrobenz-2-oxa-1,3-diazol-4-yl)amino group attached to the 2-position thereof is used.

Further, the method described in claim 14 is characterized in that in the method described in claim 10, as the D-glucose derivative that has a fluorescent chromophore in the molecule and is specifically incorporated into cells, a D-glucose derivative that has a 2-(N-methylamino)benzoylamino group in the molecule is used.

Further, the method described in claim 15 is characterized in that in the method described in claim 14, as the D-glucose derivative that has a 2-(N-methylamino)benzoylamino group in the molecule, D-deoxyglucose having a 2-(N-methylamino)benzoylamino group attached to the 2-position thereof is used.

Further, the method described in claim 16 is characterized in that in the method described in claim 12 or 14, as the L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells, an L-glucose derivative having sulforhodamine attached thereto is used.

Further, the method described in claim 17 is characterized in that in the method described in claim 12, as the L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells, an L-glucose derivative that has a 2-(N-methylamino)benzoylamino group in the molecule is used.

Further, the method described in claim 18 is characterized in that in the method described in claim 17, as the L-glucose derivative that has a 2-(N-methylamino)benzoylamino group in the molecule, L-deoxyglucose having a 2-(N-methylamino)benzoylamino group attached to the 2-position thereof is used.

Further, the method described in claim 19 is characterized in that in the method described in claim 14, as the L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells, an L-glucose derivative that has an N-(7-nitrobenz-2-oxa-1,3-diazol-4-yl)amino group in the molecule is used.

Further, the method described in claim 20 is characterized in that in the method described in claim 19, as the L-glucose derivative that has an N-(7-nitrobenz-2-oxa-1,3-diazol-4-yl) amino group in the molecule, L-deoxyglucose having an N-(7-nitrobenz-2-oxa-1,3-diazol-4-yl)amino group attached to the 2-position thereof is used.

Further, the method described in claim 21 is characterized in that in the method described in claim 10, as the L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells, two or more kinds of L-glucose derivatives, each of which has a different fluorescent chromophore in the molecule, are mixed and the resulting mixture is used.

Further, the L-glucose derivative according to the present invention is characterized by having a fluorescent chromophore in the molecule as described in claim 22.

Further, the method for producing an L-glucose derivative that has a fluorescent chromophore in the molecule according to the present invention is characterized by comprising introducing the fluorescent chromophore at the 2-position of L-glucosamine or a salt thereof obtained by acetylating the five hydroxy groups of L-mannose, substituting the acetoxy group at the 1-position by bromine, introducing an ortho ester group at the 1- and 2-positions, converting the acetyl group at each of the 3-, 4-, and 5-positions into a benzyl group, removing the ortho ester group at the 1- and 2-positions and converting into a methoxy group at the 1-position and a hydroxy group at the 2-position, respectively, trifluoromethanesulfonylating or methanesulfonylating the hydroxy group at the 2-position, followed by azidation, subjecting the azide group to hydrogen reduction, and at the same time, removing the benzyl groups, and finally converting the methoxy group at the 1-position into a hydroxy group as described in claim 23.

Further, the method for producing L-glucosamine or a salt thereof according to the present invention is characterized by comprising acetylating the five hydroxy groups of L-mannose, substituting the acetoxy group at the 1-position by bromine, introducing an ortho ester group at the 1- and 2-positions, converting the acetyl group at each of the 3-, 4-, and 5-positions into a benzyl group, removing the ortho ester group at the 1- and 2-positions and converting into a methoxy group at the 1-position and a hydroxy group at the 2-position, respectively, trifluoromethanesulfonylating or methanesulfonylating the hydroxy group at the 2-position, followed by azidation, subjecting the azide group to hydrogen reduction, and at the same time, removing the benzyl groups, and finally converting the methoxy group at the 1-position into a hydroxy group as described in claim 24.

Further, the invention is directed to the use of L-glucosamine or a salt thereof for producing an L-glucose derivative that has a fluorescent chromophore in the molecule as described in claim 25.

Effect of the Invention

According to the present invention, a method for accurately evaluating the specific incorporation of D-glucose into cells can be provided.

BRIEF DESCRIPTION OF THE DRAWINGS

The patent or application file contains at least one drawing executed in color. Copies of this patent or patent application publication with the color drawing(s) will be provided by the Office upon request and payment of the necessary fee.

MODE FOR CARRYING OUT THE INVENTION

Figure 1:
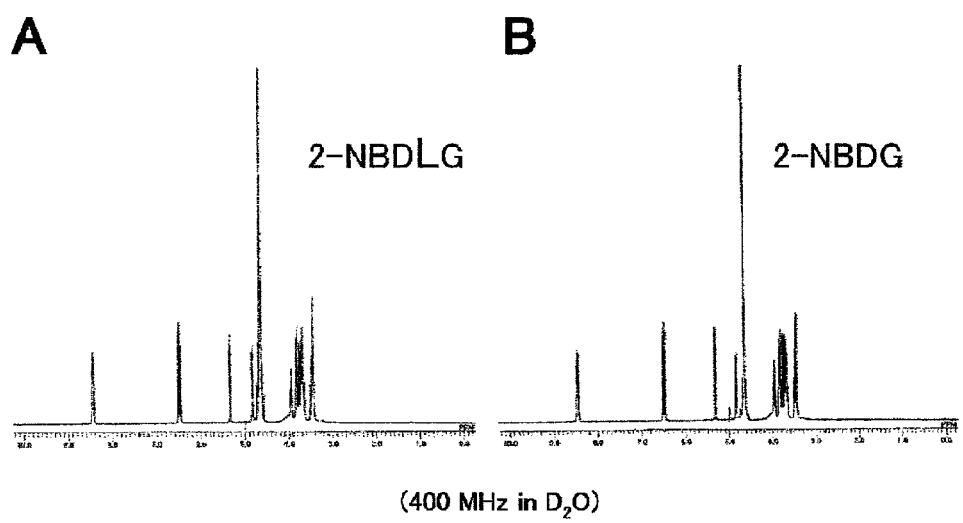
[FIG. 1] $^1$H-NMR charts of 2-NBDG and 2-NBDLG.

The method for evaluating the specific incorporation of D-glucose into cells according to the present invention can be divided into the following two methods.

(1) A method comprising contacting a D-glucose derivative that has a fluorescent chromophore in the molecule and is specifically incorporated into cells and an L-glucose derivative that has a fluorescent chromophore in the molecule with different cells in the same cell strain to be evaluated, respectively, comparing the fluorescence emitted by the D-glucose derivative that has a fluorescent chromophore in the molecule and is specifically incorporated into cells with the fluorescence emitted by the L-glucose derivative that has a fluorescent chromophore in the molecule, and evaluating the specific incorporation of D-glucose into cells relative to L-glucose by taking the difference between the two kinds of fluorescence intensities.

(2) A method comprising contacting a mixture of a D-glucose derivative that has a fluorescent chromophore in the molecule and is specifically incorporated into cells and an L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells with cells to be evaluated, and detecting the fluorescence emitted by the D-glucose derivative that has a fluorescent chromophore in the molecule and is specifically incorporated into cells.

Hereinafter, the above methods will be described, respectively.

(1) The method comprising contacting a D-glucose derivative that has a fluorescent chromophore in the molecule and is specifically incorporated into cells and an L-glucose derivative that has a fluorescent chromophore in the molecule with different cells in the same cell strain to be evaluated, respectively, comparing the fluorescence emitted by the D-glucose derivative that has a fluorescent chromophore in the molecule and is specifically incorporated into cells with the fluorescence emitted by the L-glucose derivative that has a fluorescent chromophore in the molecule, and evaluating the specific incorporation of D-glucose into cells relative to L-glucose by taking the difference between the two kinds of fluorescence intensities.

In this method, the D-glucose derivative (which may be in the form of a salt such as a hydrochloride salt) that has a fluorescent chromophore in the molecule and is specifically incorporated into cells means a compound that is a D-glucose derivative having a fluorescent chromophore in the molecule and is incorporated into cells in a specific manner when compared to L-glucose or a derivative thereof (such as L-glucosamine or L-deoxyglucose), and specific examples thereof include D-glucose derivatives having an N-(7-nitrobenz-2-oxa-1,3-diazol-4-yl)amino group in the molecule such as 2-NBDG described in Non-patent documents 1 and 2 and D-deoxyglucose having an N-(7-nitrobenz-2-oxa-1,3-diazol-4-yl)amino group attached to the 6-position thereof (6-[N-(7-nitrobenz-2-oxa-1,3-diazol-4-yl)amino]-6-deoxy-D-glucose: 6-NBDG: Speizer L. et al., Biochim. Biophys. Acta 815: 75-84, 1985).

The L-glucose derivative (which may be in the form of a salt such as a hydrochloride salt) that has a fluorescent chromophore in the molecule is a compound that is basically not specifically incorporated into cells because it is an L-form and can be used as a control for the D-glucose derivative that has a fluorescent chromophore in the molecule and is specifically incorporated into cells such as 2-NBDG in the present invention. Specific examples thereof include L-glucose derivatives having an N-(7-nitrobenz-2-oxa-1,3-diazol-4-yl) amino group in the molecule such as L-deoxyglucose having an N-(7-nitrobenz-2-oxa-1,3-diazol-4-yl)amino group attached to the 2-position thereof (2-[N-(7-nitrobenz-2-oxa-1,3-diazol-4-yl)amino]-2-deoxy-L-glucose: 2-NBDLG) and L-deoxyglucose having an N-(7-nitrobenz-2-oxa-1,3-diazol-4-yl)amino group attached to the 6-position thereof (6-[N-(7-nitrobenz-2-oxa-1,3-diazol-4-yl)amino]-6-deoxy-L-glucose: 6-NBDLG).

For example, 2-NBDLG, as shown below, is in an enantiomeric relationship with 2-NBDG, and both have the same physicochemical properties except for the sign of optical rotation.

[Chemical 2]

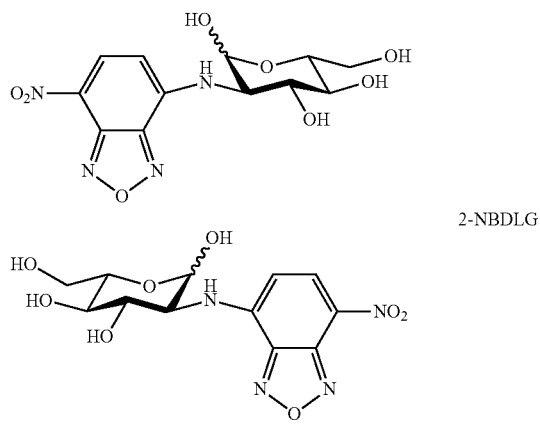

Accordingly, the nonspecific adsorption property of 2-NBDLG onto the surface of the cell membrane or in the membrane, nonspecific incorporation thereof into cells without being mediated by a glucose transporter, and the like are considered to be the same as or at least equivalent to those of 2-NBDG. Therefore, in the case where the fluorescence intensity obtained by the administration of 2-NBDG includes the fluorescence emitted by 2-NBDG nonspecifically adsorbed onto the surface of the cell membrane or in the membrane, 2-NBDG nonspecifically incorporated into cells without being mediated by a glucose transporter, and the like, a fluorescence intensity that is at least equivalent to the fluorescence intensity derived from such fluorescence can be obtained also by the administration of 2-NBDLG serving as the control. So, by comparing the fluorescence emitted by 2-NBDG with the fluorescence emitted by 2-NBDLG and obtaining a difference in the fluorescence intensity between the two kinds of glucose derivatives through observation, quantification, and the like, the difference can be evaluated as the specific incorporation of 2-NBDG into cells relative to 2-NBDLG, namely, as the specific incorporation of D-glucose into cells relative to L-glucose.

Incidentally, in this method, it is not preferable that due to a difference between the chemical structure of the fluorescent chromophore of the D-glucose derivative that has a fluorescent chromophore in the molecule and is specifically incorporated into cells and the chemical structure of the fluorescent chromophore of the L-glucose derivative that has a fluorescent chromophore in the molecule, the physicochemical properties of the two kinds of glucose derivatives vary greatly. Therefore, the chemical structures of the fluorescent chromophores of the two kinds of glucose derivatives are preferably completely the same or are the same except for a substituent which may be contained as a side chain.

Further, in principle, because this method is performed by contacting the D-glucose derivative that has a fluorescent chromophore in the molecule and is specifically incorporated into cells and the L-glucose derivative that has a fluorescent chromophore in the molecule with different cells in the same cell strain to be evaluated, respectively (a difference in the fluorescence intensity cannot be obtained, if both glucose derivatives are simultaneously administered to one cell), it is preferred that the activities of the cells to which the glucose derivatives are administered respectively are the same or at least equivalent to each other. In order to ensure this condition, it is preferred to confirm the activities of the cells during experiment. Examples of a method for confirming the activities of the cells include a method for confirming that the cell membrane potential is normal using a patch clamp technique or the like, and a method for measuring an action potential (these methods are preferred in the case of neurons) and a method for measuring the metabolic activity. Alternatively, the number of cells with which the D-glucose derivative that has a fluorescent chromophore in the molecule and is specifically incorporated into cells and the L-glucose derivative that has a fluorescent chromophore in the molecule are contacted, respectively, can be set to more than 1 (n≥2), and a statistical analysis may be performed.

The L-glucose derivative that has a fluorescent chromophore in the molecule can be produced by introducing the fluorescent chromophore into L-glucose or a derivative thereof (such as L-glucosamine or L-deoxyglucose). L-glucosamine or a salt thereof (such as a hydrochloride salt) that is useful for the production of the L-glucose derivative that has a fluorescent chromophore in the molecule can be obtained by, for example, acetylating the five hydroxy groups of L-mannose, substituting the acetoxy group at the 1-position by bromine, introducing an ortho ester group at the 1- and 2-positions, converting the acetyl group at each of the 3-, 4-, and 5-positions into a benzyl group, removing the ortho ester group at the 1- and 2-positions and converting into a methoxy group at the 1-position and a hydroxy group at the 2-position, respectively, trifluoromethanesulfonylating or methanesulfonylating the hydroxy group at the 2-position, followed by azidation, subjecting the azide group to hydrogen reduction, and at the same time, removing the benzyl groups, and finally converting the methoxy group at the 1-position into a hydroxy group.

Incidentally, a combination of the D-glucose derivative that has a fluorescent chromophore in the molecule and is specifically incorporated into cells with the L-glucose derivative that has a fluorescent chromophore in the molecule which can be used in this method is not limited to a combination of the above-mentioned D-glucose derivative that has an N-(7-nitrobenz-2-oxa-1,3-diazol-4-yl)amino group in the molecule and emits green fluorescence (such as 2-NBDG) with the L-glucose derivative that has an N-(7-nitrobenz-2-oxa-1,3-diazol-4-yl)amino group in the molecule and emits green fluorescence (such as 2-NBDLG), and it may be a combination of a D-glucose derivative that has a 2-(N-methylamino) benzoylamino group in the molecule and emits blue fluorescence with an L-glucose derivative that has a 2-(N-methylamino)benzoylamino group in the molecule and emits blue fluorescence, or the like. Examples of the D-glucose derivative that has a 2-(N-methylamino)benzoylamino group in the molecule include D-deoxyglucose having a 2-(N-methylamino)benzoylamino group attached to the 2-position thereof (2-[N-2-(N'-methylamino)benzoylamino]-2-deoxy-D-glucose: 2-NMAG), and examples of the L-glucose derivative that has a 2-(N-methylamino)benzoylamino group in the molecule include L-deoxyglucose having a 2-(N-methylamino)benzoylamino group attached to the 2-position thereof (2-[N-2-(N'-methylamino)benzoylamino]-2-deoxy-L-glucose: 2-NMALG).

(2) The method comprising contacting a mixture of a D-glucose derivative that has a fluorescent chromophore in the molecule and is specifically incorporated into cells and an L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells with cells to be evaluated, and detecting the fluorescence emitted by the D-glucose derivative that has a fluorescent chromophore in the molecule and is specifically incorporated into cells.

In this method, the D-glucose derivative (which may be in the form of a salt such as a hydrochloride salt) that has a fluorescent chromophore in the molecule and is specifically incorporated into cells means a compound that is a D-glucose derivative having a fluorescent chromophore in the molecule and is incorporated into cells in a specific manner when compared to L-glucose or a derivative thereof (such as L-glucosamine or L-deoxyglucose), and specific examples thereof include D-glucose derivatives having an N-(7-nitrobenz-2-oxa-1,3-diazol-4-yl)amino group in the molecule such as 2-NBDG described in Non-patent documents 1 and 2 and D-deoxyglucose having an N-(7-nitrobenz-2-oxa-1,3-diazol-4-yl)amino group attached to the 6-position thereof (6-[N-(7-nitrobenz-2-oxa-1,3-diazol-4-yl)amino]-6-deoxy-D-glucose: 6-NBDG: Speizer L. et al., Biochim. Biophys. Acta 815: 75-84, 1985).

Examples of the L-glucose derivative (which may be in the form of a salt such as a hydrochloride salt) that has, in the molecule, a fluorescent chromophore that emits fluorescence at a wavelength different from that of the fluorescence emitted by the D-glucose derivative that has a fluorescent chromophore in the molecule and is specifically incorporated into cells include L-glucose derivatives having sulforhodamine (such as sulforhodamine B, sulforhodamine G, or sulforhodamine 101) attached thereto, and specific examples thereof include L-deoxyglucose having sulforhodamine 101 attached to the 2-position thereof via a sulfonamide bond (referred to as 2-TRLG).

When the case where a mixed liquid of 2-NBDG and 2-TRLG was used as the mixed liquid of a D-glucose derivative that has a fluorescent chromophore in the molecule and is specifically incorporated into cells and an L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells is cited as an example, the maximum fluorescence wavelength of the former is from 540 nm to 550 nm, and the maximum fluorescence wavelength of the latter is from 600 nm to 610 nm. Therefore, when the fluorescence at a wavelength in the vicinity of each of the maximum fluorescence wavelengths is detected for the solution obtained by mixing both glucose derivatives, the green fluorescence emitted by 2-NBDG and the red fluorescence emitted by 2-TRLG can be detected, respectively, and as a result of combining the both fluorescence spectra detected, yellow fluorescence can be detected. After administration of the mixed liquid of 2-NBDG and 2-TRLG to cells, when 2-NBDG is specifically incorporated into the cells, green fluorescence is detected from the inside of the cells. On the other hand, in the case where a part of the cell membrane is disrupted or in the case where even if the cell membrane is not disrupted, the membrane is in a state where glucose or a derivative thereof is nonspecifically incorporated, both 2-NBDG and 2-TRLG are incorporated into the cells, and hence yellow fluorescence is detected from the inside of the cells. Therefore, by detecting the green fluorescence emitted by 2-NBDG after the mixed liquid of 2-NBDG and 2-TRLG is administered to cells, the specific incorporation of D-glucose into cells relative to L-glucose can be accurately evaluated in real time.

Incidentally, this method utilizes a difference in the wavelength between the fluorescence emitted by the D-glucose derivative that has a fluorescent chromophore in the molecule and is specifically incorporated into cells and the fluorescence emitted by the L-glucose derivative that has a fluorescent chromophore in the molecule, and therefore, the larger the difference in the maximum fluorescence wavelength between the two kinds of glucose derivatives, the easier and more accurately the difference can be discriminated. Accordingly, it is preferred that the difference in the maximum fluorescence wavelength between both glucose derivatives is at least 20 nm. In the case where 2-NBDG is used as the D-glucose derivative that has a fluorescent chromophore in the molecule and is specifically incorporated into cells, as the L-glucose derivative that has a fluorescent chromophore in the molecule, an L-glucose derivative that has a 7-(N,N-dimethylaminosulfonyl)benz-2-oxa-1,3-diazol-4-yl)amino group in the molecule, specifically, L-deoxyglucose having a 7-(N,N-dimethylaminosulfonyl)benz-2-oxa-1,3-diazol-4-yl) amino group attached to the 2-position thereof (2-[N-7-(N',N'-dimethylaminosulfonyl)benz-2-oxa-1,3-diazol-4-yl)amino]-2-deoxy-L-glucose: 2-DBDLG) can also be used (the fluorescence thereof is yellow to yellow green, and the maximum fluorescence wavelength thereof is from 570 nm to 580 nm). Further, as the L-glucose derivative that has a fluorescent chromophore in the molecule, an L-glucose derivative that has a 2-(N-methylamino)benzoylamino group in the molecule, specifically, L-deoxyglucose having a 2-(N-methylamino)benzoylamino group attached to the 2-position thereof (2-[N-2-(N'-methylamino)benzoylamino]-2-deoxy-L-glucose: 2-NMALG) can also be used (the fluorescence thereof is blue, and the maximum fluorescence wavelength thereof is from 450 nm to 460 nm).

Further, as the D-glucose derivative that has a fluorescent chromophore in the molecule and is specifically incorporated into cells, a D-glucose derivative that has a 2-(N-methylamino)benzoylamino group in the molecule, specifically, D-deoxyglucose having a 2-(N-methylamino)benzoylamino group attached to the 2-position thereof (2-[N-2-(N'-methylamino)benzoylamino]-2-deoxy-D-glucose: 2-NMAG) can also be used (the fluorescence thereof is blue, and the maximum fluorescence wavelength thereof is from 450 nm to 460 nm). In this case, as the L-glucose derivative that has a fluorescent chromophore in the molecule, 2-NBDLG or 2-TRLG can be used.

Further, in the case where there is a difference in the intensity between the fluorescence emitted by the D-glucose derivative that has a fluorescent chromophore in the molecule and is specifically incorporated into cells and the fluorescence emitted by the L-glucose derivative that has a fluorescent chromophore in the molecule, it is preferred that the mixing ratio of both glucose derivatives is adjusted within a range of, for example from 1:100 to 100:1 (molar ratio) such that the intensities of the fluorescence spectra emitted by the both glucose derivatives are equivalent to each other.

Incidentally, in this method, as the L-glucose derivative that has, in the molecule, a fluorescent chromophore that emits fluorescence at a wavelength different from that of the fluorescence emitted by the D-glucose derivative that has a fluorescent chromophore in the molecule and is specifically incorporated into cells, two or more kinds of L-glucose derivatives, each of which has a different fluorescent chromophore in the molecule, may be mixed and used (for example, a combination of 2-TRLG and 2-NMALG, or the like). By mixing and using two or more kinds of L-glucose derivatives, each of which has a different fluorescent chromophore in the molecule, for example, a difference in the nonspecifically incorporated L-glucose derivative based on a difference in the degree of the deterioration state of the cell membrane can be detected, and therefore, the specific incorporation of D-glucose into cells relative to L-glucose can be evaluated and also the degree of the deterioration state of the cell membrane can be evaluated by the method.

The experimental condition for evaluating the specific incorporation of D-glucose into cells of the present invention may be according to known condition (if necessary, see Non-patent document 2).

In the method for evaluating the specific incorporation of D-glucose into cells of the present invention, other than cells (such as neurons) in any region in mammals including humans, cells of microbial such as *Escherichia coli* and yeast, plant cells, fertilized eggs, and the like can be used as evaluation targets, and the method contributes to the advancement of the research as to how organisms incorporate D-glucose into cells and utilize it, and also the usefulness of the method is expected in the medical field, hygiene field, and other field for distinguishing normal cells from tumor cells based on a difference in the degree of the incorporation of D-glucose or for preventing or controlling microbial contamination (counting of the number of microorganisms, evaluation for the state thereof, etc.). Incidentally, when the specific incorporation of D-glucose into cells is evaluated, any of the above two methods may be selected, however, by performing the both methods in combination, more accurate evaluation can be performed.

EXAMPLES

Hereinafter, the present invention will be described in detail with reference to Examples, however, the present invention is not construed as being limited to the following description.

Example 1

Example of Applying 2-NBDG or 2-NBDLG to Neurons 1-1: Synthesis of 2-NBDG

The synthesis of 2-NBDG was performed according to the method described in Non-patent document 1.

1-2: Synthesis of 2-NBDLG (A) Synthesis of L-Glucosamine Hydrochloride

The synthesis of L-glucosamine hydrochloride was performed according to the following pathway.

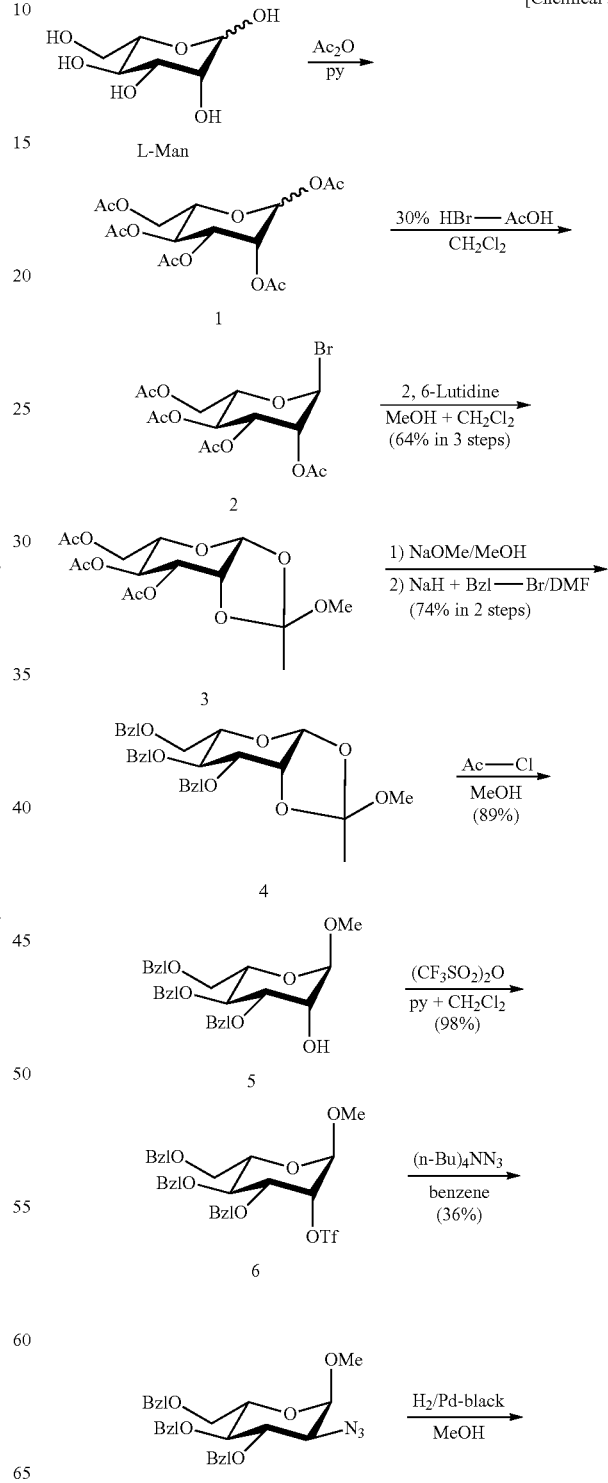

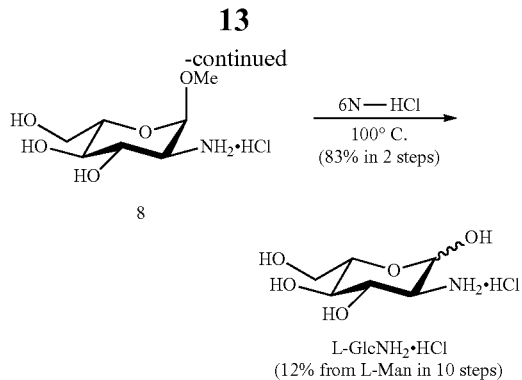

L-GlcNH$_2$·HCl
(12% from L-Man in 10 steps)

(1) Synthesis of 1,2,3,4,6-penta-O-acetyl-L-mannopyranose (1)

L-(−)-mannose (9.0 g, 49.96 mmol) was dissolved in pyridine (120 ml), and the resulting solution was cooled in ice. Acetic anhydride (60 ml) was added dropwise thereto over about 15 minutes. The resulting solution was stirred overnight while gradually returning to room temperature. Thereafter, the reaction mixture was concentrated under reduced pressure. Toluene was added to the resulting residue, and an azeotropic distillation procedure was performed twice. Ethyl acetate was added to the residue to dissolve the residue, and the resulting solution was washed sequentially with saturated NaHCO$_3$ solution, water, and saturated saline. The organic layer was dried over anhydrous magnesium sulfate and filtered, and the filtrate was concentrated under reduced pressure. The obtained residue was dried well under reduced pressure, whereby a target product was obtained (crude yield: 21.04 g (which exceeded the theoretical yield because ethyl acetate and the like were contained, and therefore, the molar amount thereof was taken as 49.96 mmol, and the subsequent reaction was performed)).

$^1$H-NMR spectrum (400 MHz, CDCl$_3$, δ, ppm): 6.10 (d, 1H, J=1.9 Hz, H-1), 5.26-5.36 (m, 3H, H-2, H-3, and H-4), 4.29 (dd, 1H, J=5.0 and 12.3 Hz, H-6a), 4.11 (dd, 1H, J=2.4 Hz and 12.3 Hz, H-6b), 4.06 (m, 1H, H-5), 2.19 (s, 3H, Ac), 2.18 (s, 3H, Ac), 2.11 (s, 3H, Ac), 2.06 (s, 3H, Ac), 2.02 (s, 3H, Ac)

(2) Synthesis of 2,3,4,6-tetra-O-acetyl-α-L-mannopyranosyl bromide (2)

1,2,3,4,6-penta-O-acetyl-L-mannopyranose (1) (21.04 g) was dissolved in dehydrated dichloromethane (150 ml), and the resulting solution was cooled in ice. 30% HBr/AcOH (27.5 ml) was added dropwise thereto over about 10 minutes, and after completion of the dropwise addition, the ice bath was removed, and the mixture was stirred at room temperature for 3 hours. The reaction mixture was concentrated under reduced pressure. Toluene was added to the resulting residue, and an azeotropic distillation procedure was performed twice. Ethyl acetate was added to the residue to dissolve the residue, and the resulting solution was washed sequentially with saturated NaHCO$_3$ solution, water, and saturated saline. The organic layer was dried over anhydrous magnesium sulfate and filtered, and the filtrate was concentrated under reduced pressure. The obtained residue was dried well under reduced pressure, whereby a target product was obtained (crude yield: 21.45 g (which exceeded the theoretical yield because ethyl acetate and toluene were contained, and therefore, the molar amount thereof was taken as 49.96 mmol, and the subsequent reaction was performed)).

$^1$H-NMR spectrum (400 MHz, CDCl$_3$, δ, ppm): 6.30 (d, 1H, J=1.5 Hz, H-1), 5.72 (dd, 1H, J=3.6 Hz and 10.3 Hz, H-3), 5.46 (dd, 1H, J=1.5 Hz and 3.6 Hz, H-2), 5.38 (dd, 1H, J=10.3 Hz and 10.3 Hz, H-4), 4.34 (dd, 1H, J=4.9 Hz and 12.5 Hz, H-6a), 4.22 (ddd, 1H, J=2.1 Hz, 4.9 Hz, and 10.3 Hz, H-5), 4.15 (dd, 1H, J=2.1 Hz and 12.5 Hz, H-6b), 2.18 (s, 3H, Ac), 2.11 (s, 3H, Ac), 2.08 (s, 3H, Ac), 2.02 (s, 3H, Ac)

(3) Synthesis of 3,4,6-tri-O-acetyl-β-L-mannopyranose 1,2-(methyl orthoacetate) (3)

2,3,4,6-tetra-O-acetyl-α-L-mannopyranosyl bromide (2) (21.45 g) was dissolved in dehydrated dichloromethane (120 ml). Under an argon atmosphere, 2,6-lutidine (15.73 ml)/dehydrated methanol (120 ml) was added dropwise thereto over about 30 minutes. The resulting mixture was stirred overnight at room temperature under an argon atmosphere. After 24 hours, the reaction mixture was diluted with dichloromethane, and the resulting solution was washed sequentially with saturated NaHCO$_3$ solution and water. The organic layer was concentrated under reduced pressure. Toluene was added to the resulting residue, and an azeotropic distillation procedure was performed three times. The residue was dissolved in methanol (100 ml), and then, water (800 ml) was added thereto in small portions. The precipitated crystals were obtained by filtration, washed with water, and dried well under reduced pressure (1st, 8.92 g). Subsequently, the 1st filtrate and the washing solution were combined, and the resulting mixture was concentrated under reduced pressure to reduce the amount of the liquid. The precipitated crystals were obtained by filtration, washed with water, and dried well under reduced pressure (2nd, 2.62 g), whereby a target product was obtained (overall yield: 11.54 g (overall yield ratio by three steps based on the amount of L-(−)-mannose: 64%)).

$^1$H-NMR spectrum (400 MHz, CDCl$_3$, δ, ppm): 5.50 (d, 1H, J=2.8 Hz, H-1), 5.31 (dd, 1H, J=9.4 Hz and 10.0 Hz, H-4), 5.15 (dd, 1H, J=3.9 Hz and 10.0 Hz, H-3), 4.62 (dd, 1H, J=2.8 Hz and 3.9 Hz, H-2), 4.24 (dd, 1H, J=4.9 Hz and 12.2 Hz, H-6a), 4.15 (dd, 1H, J=3.0 Hz and 12.2 Hz, H-6b), 3.69 (ddd, 1H, J=3.0 Hz, 4.9 Hz and 9.4 Hz, H-5), 2.13 (s, 3H, Ac), 2.08 (s, 3H, Ac), 2.06 (s, 3H, Ac), 1.75 (s, 3H, Me)

(4) Synthesis of 3,4,6-tri-O-benzyl-β-L-mannopyranose 1,2-(methyl orthoacetate) (4)

3,4,6-tri-O-acetyl-β-L-mannopyranose 1,2-(methyl orthoacetate) (3) (11.52 g) was dissolved in methanol (200 ml), and a solution of 5.2 M NaOMe in methanol (184 μl) was added thereto. After the resulting solution was stirred at room temperature for 1 hour, Amberlyst 15 was added thereto to neutralize the solution, followed by filtration. The resin was washed with methanol, and the filtrate and the washing solution were combined, and the resulting mixture was concentrated under reduced pressure. The obtained residue was dried well under reduced pressure. The total amount of the dried residue was dissolved in dried DMF (100 ml), and the resulting solution was cooled in ice. Sodium hydride (NaH) (a 60% oil suspension, 7.38 g) was added thereto in small portions. After foaming due to the generation of hydrogen was stopped, benzyl bromide (12.1 ml) was added dropwise thereto. The resulting solution was stirred overnight while gradually returning to room temperature. The reaction mixture was cooled in ice, and in order to decompose the excess NaH, methanol was added thereto in small portions until foaming was no longer observed. The resulting solution was diluted by adding chloroform thereto, and the obtained solution was washed sequentially with water and saturated saline. The organic layer was dried over anhydrous magnesium sulfate and filtered, and the filtrate was concentrated under reduced pressure. The obtained residue was dried well under reduced pressure, and the dried residue was stored overnight in a freezer. On the next morning, the stored residue was separated into precipitates and oil. The oil (unnecessary substance) was removed using a Pasteur pipette. The precipitates (wet weight: 17.97 g) was purified by silica gel column chromatography, whereby a target product was obtained (yield: 11.98 g, yield ratio: 74%).

$^1$H-NMR spectrum (400 MHz, CDCl$_3$, δ, ppm): 7.22-7.41 (m, 15H, Ph), 5.35 (d, 1H, J=2.5 Hz), 4.79 (ABq, 2H, J=12.4 Hz, CH$_2$-Ph), 4.75 (ABq, 2H, J=11.0 Hz, CH$_2$-Ph), 4.58 (ABq, 2H, J=12.4 Hz, CH$_2$-Ph), 4.40 (dd, 1H, J=2.5 Hz and 4.1 Hz, H-2), 3.92 (dd, 1H, J=9.7 Hz and 9.7 Hz, H-4), 3.69-3.77 (m, 3H, H-3, H-6a, and H-6b), 3.42 (ddd, 1H, J=2.3 Hz, 4.5 Hz, and 9.7 Hz, H-5), 3.29 (s, 3H, OMe), 1.74 (s, 3H, Me)

(5) Synthesis of methyl 3,4,6-tri-O-benzyl-α-L-mannopyranoside (5)

3,4,6-tri-O-benzyl-β-L-mannopyranose 1,2-(methyl orthoacetate) (4) (11.98 g) was dissolved in dehydrated methanol (240 ml), and the resulting solution was stirred while heating at 65° C. Acetyl chloride (6.73 ml) was added dropwise thereto, and after completion of the dropwise addition, the set temperature of the oil bath was changed to 75° C. and the mixture was brought to reflux by heating. After 3 hours, the heating of the oil bath was switched off, and the mixture was stirred overnight. The reaction mixture was concentrated under reduced pressure, and chloroform was added to the resulting residue to dissolve the residue. Then, the obtained solution was washed sequentially with saturated NaHCO$_3$ solution, water, and saturated saline. The organic layer was dried over anhydrous magnesium sulfate and filtered, and the filtrate was concentrated under reduced pressure. The obtained residue was purified by silica gel column chromatography, whereby a target product was obtained (yield: 9.74 g, yield ratio: 89%).

$^1$H-NMR spectrum (400 MHz, CDCl$_3$, δ, ppm): 7.24-7.36 (m, 15H, Ph), 4.80 (d, 1H, J=1.6 Hz, H-1), 4.69 (ABq, 2H, J=11.9 Hz, CH$_2$-Ph), 4.67 (ABq, 2H, J=11.3 Hz, CH$_2$-Ph), 4.60 (ABq, 2H, J=12.4 Hz, CH$_2$-Ph), 4.03 (m, 1H, H-2), 3.70-3.88 (m, 5H, H-3, H-4, H-5, H-6a and H-6b), 3.37 (s, 3H, OMe), 2.49 (br.d, 1H, J=2.5 Hz, O$_2$—OH)

(6) Synthesis of methyl 3,4,6-tri-O-benzyl-2-O-trifluoromethanesulfonyl-α-L-mannopyranoside (6)

Methyl 3,4,6-tri-O-benzyl-α-L-mannopyranoside (5) (9.74 g) was dissolved in dehydrated dichloromethane (220 ml), pyridine (4.24 ml) was added thereto, and the resulting mixture was cooled to −15° C. under an argon atmosphere. Trifluoromethanesulfonic acid anhydride (5.29 ml) was added thereto, and the resulting mixture was stirred at room temperature. After 1 hour, saturated NaHCO$_3$ solution was added to the reaction mixture, and extraction was performed with dichloromethane. The organic layers were combined, and the combined organic layer was washed sequentially with saturated NaHCO$_3$ solution, water, and saturated saline. The organic layer was dried over anhydrous magnesium sulfate and filtered, and the filtrate was concentrated under reduced pressure. Toluene was added to the resulting residue, and an azeotropic distillation procedure was performed three times. The obtained residue was purified by silica gel column chromatography, whereby a target product was obtained (yield: 12.23 g, yield ratio: 98%).

$^1$H-NMR spectrum (400 MHz, CDCl$_3$, δ, ppm): 7.10-7.38 (m, 15H, Ph), 5.11 (m, 1H, H-2), 4.90 (d, 1H, J=1.9 Hz, H-1), 4.69 (ABq, 2H, J=12.0 Hz, CH$_2$-Ph), 4.64 (ABq, 2H, J=10.7 Hz, CH$_2$-Ph), 4.61 (ABq, 2H, J=11.7 Hz, CH$_2$-Ph), 4.00 (dd, 1H, J=2.9 Hz and 8.9 Hz, H-3), 3.69-3.84 (m, 4H, H-4, H-5, H-6a and H-6b), 3.40 (s, 3H, OMe)

(7) Synthesis of methyl 2-azido-3,4,6-tri-O-benzyl-2-deoxy-α-L-glucopyranoside (7)

Methyl 3,4,6-tri-O-benzyl-2-O-trifluoromethanesulfonyl-α-L-mannopyranoside (6) (12.23 g) was dissolved in dehydrated benzene (400 ml), tetrabutylammonium azide [(n-Bu)$_4$NN$_3$] (29.16 g) was added thereto under an argon atmosphere. After 3 days, (n-Bu)$_4$NN$_3$ (3.61 g) was further added thereto. The mixture was stirred at room temperature for an additional 11 days (14 days in total). The reaction mixture was charged to a silica gel column as such to effect purification by silica gel column chromatography combined with preparative thin-layer chromatography, whereby a target product was obtained (yield: 3.58 g, yield ratio: 36%).

$^1$H-NMR spectrum (400 MHz, CDCl$_3$, δ, ppm): 7.15-7.38 (m, 15H, Ph), 4.87 (ABq, 2H, J=12.4 Hz, CH$_2$-Ph), 4.83 (d, 1H, J=3.5 Hz, H-1), 4.66 (ABq, 2H, J=10.7 Hz, CH$_2$-Ph), 4.57 (ABq, 2H, J=12.4 Hz, CH$_2$-Ph), 3.98 (dd, 1H, J=8.9 Hz and 10.2 Hz, H-3), 3.66-3.80 (m, 4H, H-4, H-5, H-6a, and H-6b), 3.45 (dd, 1H, J=3.5 Hz and 10.4 Hz, H-2), 3.43 (s, 3H, OMe)

(8) Synthesis of methyl 2-amino-2-deoxy-α-L-glucopyranoside hydrochloride (8)

Methyl 2-azido-3,4,6-tri-O-benzyl-2-deoxy-α-L-glucopyranoside (7) (1.98 g, 4.04 mmol) was dissolved in methanol (70 ml), 1 M HCl (4.85 ml) and palladium black (500 mg) were added thereto, and the resulting mixture was subjected to catalytic reduction by pressurization to 8 atm. After 22 hours, the pressure was returned to normal, and after it was confirmed that only one spot was detected by TLC, the catalyst was removed by filtration. The catalyst was washed with methanol, and the filtrate and the washing solution were combined, and the resulting mixture was concentrated under reduced pressure. Water was added to the obtained residue, and a concentration procedure under reduced pressure was performed twice. The obtained residue was dissolved in water and the resulting solution was lyophilized, whereby a target product was obtained (crude yield: 963 mg (which exceeded the theoretical yield because water and hydrochloric acid were contained, and therefore, the remaining amount thereof (960 mg) after a portion thereof was used for $^1$H-NMR measurement was taken as 4.03 mmol, and the subsequent reaction (final step of deprotection) was performed)).

$^1$H-NMR spectrum (400 MHz, D$_2$O, δ, ppm): 4.89 (d, 1H, J=3.7 Hz, H-1), 3.75 (dd, 1H, J=2.5 Hz and 12.3 Hz, H-6a), 3.72 (dd, 1H, J=9.2 Hz and 10.5 Hz, H-3), 3.66 (dd, 1H, J=5.2 Hz and 12.3 Hz, H-6b), 3.57 (ddd, 1H, J=2.5 Hz, 5.2 Hz, and 9.8 Hz, H-5), 3.35 (dd, 1H, J=9.2 Hz and 9.8 Hz, H-4), 3.31 (s, 3H, OMe), 3.20 (dd, 1H, J=3.7 Hz and 10.5 Hz, H-2)

(9) Synthesis of L-glucosamine hydrochloride (L-GlcNH$_2$.HCl)

Methyl 2-amino-2-deoxy-α-L-glucopyranoside hydrochloride (8) (960 mg, calculated to be equivalent to 4.03 mmol) was dissolved in 6 N HCl (40 ml), and the resulting solution was stirred while heating at 100° C. After the solution was allowed to react for a total of 30 hours, the solution was returned to room temperature and concentrated under reduced pressure. Water was added to the resulting residue, and a concentration procedure under reduced pressure was performed five times. The obtained residue was dissolved in water and the resulting solution was lyophilized. The obtained residue was passed through CHP-20, and the flow-through fraction was collected and lyophilized (crude yield: 805 mg (3.73 mmol, equivalent crude yield ratio: 93%)). Further, 531 mg (equivalent to 2.46 mmol) of the crude product was purified by normal phase HPLC (TSK-Gel Amide-80), and a target fraction was collected and concentrated under reduced pressure. Water was added to the resulting residue, and a lyophilization procedure was performed three times, whereby a target product was obtained (yield: 474 mg (2.20 mmol), yield ratio: 83%).

$^1$H-NMR spectrum (400 MHz, D$_2$O, δ, ppm): 5.36 [d, 0.7H, J=3.5 Hz, H-1 (α-form), 4.85 [d, 0.3H, J=8.3 Hz, H-1 (β-form)], 3.36-3.84 [m, 5H, H-3, H-4, H-5, H-6a, and H-6b (α-form and (β-form), 3.21 [dd, 0.7H, J=3.5 Hz and 10.6 Hz, H-2 (α-form), 2.92 [dd, 0.3H, J=8.3 Hz and 10.6 Hz, H-2 (β-form)]

(Elemental Analysis Result)

Calculated value: C, 33.42 (%), H, 6.54 (%), N, 6.50 (%)

Measured value (1st): C, 33.31 (%), H, 6.46 (%), N, 6.36 (%)

Measured value (2nd): C, 33.30 (%), H, 6.48 (%), N, 6.36 (%)

([α]D at 20° C.)

Measured value: −72.05 (c=1.0, H$_2$O) (at 24 hours after being dissolved in water)

(Reference data: [α]D of commercially available D-glucosamine hydrochloride at 20° C.)

Measured value: +72.20 (c=1.0, H$_2$O) (at 24 hours after being dissolved in water)

(B) Synthesis of 2-NBDLG (part 1)

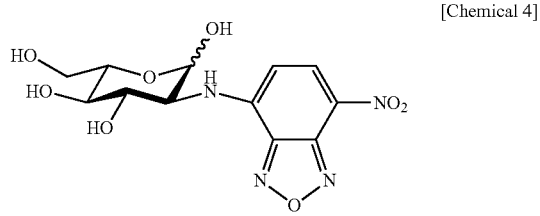

[Chemical 4]

In a brown flask, 4-chloro-7-nitro-2,1,3-benzoxadiazole (NBD-Cl) (483 mg) was placed and dissolved in methanol (14.0 ml). Under an argon atmosphere, a solution in which L-glucosamine hydrochloride (283 mg) was dissolved in 0.3 M NaHCO$_3$ solution (5.57 ml) was added thereto, and the resulting mixture was stirred at room temperature. After 24 hours, methanol was removed by concentration under reduced pressure, and the resulting precipitates (unnecessary substances derived from NBD-Cl) were removed by filtration. The precipitates were washed with water, and the filtrate and the washing solution were combined, followed by purification by HPLC. A target fraction was collected and lyophilized, whereby a target product was obtained (yield: 102 mg, yield ratio: 23%).

$^1$H-NMR spectrum (400 MHz, D$_2$O, δ, ppm): 8.52 (d, 1H, J=9.1 Hz, H6'), 6.56 and 6.54 (d×2, 0.5H×2, J=9.1 Hz and J=9.1 Hz, H5'), 5.38 [d, 0.5H, J=2.8 Hz, H-1 (α-form)], 4.89 [d, 0.5H, J=8.1 Hz, H-1 (β-form)], 3.50-4.02 (m, 6H, H-2, H-3, H-4, H-5, H-6a, and H-6b (α-form and (β-form)](see FIG. 1)

ESI-MS: calcd for C$_{12}$H$_{15}$N$_4$O$_8$ [M+H]$^+$343.1, found 343.1

(C) Synthesis of 2-NBDLG (part 2)

In a brown flask, L-glucosamine hydrochloride (40.0 mg) and NaHCO$_3$ (26.0 mg) were placed and dissolved in water (800 μl). A solution in which 4-fluoro-7-nitro-2,1,3-benzoxadiazole (NBD-F) (92.0 mg) was dissolved in methanol (4.0 ml) was added thereto, and under an argon atmosphere, the resulting mixture was stirred for 2 hours at a bath temperature of 37° C. Thereafter, the mixture was stirred at room temperature for an additional 40 minutes. Methanol was removed by concentration under reduced pressure, and the resulting precipitates (unnecessary substances derived from NBD-F) were removed by filtration. The precipitates were washed with water, and the filtrate and the washing solution were combined, followed by purification by HPLC. A target fraction was collected and lyophilized, whereby a target product was obtained (yield: 48.7 mg, yield ratio: 76%).

1-3: Application of 2-NBDG or 2-NBDLG to acutely isolated neurons (capture of images by normal fluorescence microscope)

(Application Method)

(A) Preparation of Acutely Isolated Neurons (1) Preparation of Mouse Brain Slices C57BL/6J mice at the age of 13 to 15 days after birth (juvenile period) or at the age of 33 to 45 days after birth (maturation period) were deeply anesthetized with urethane (i.p. 1.6 g/kg) and decapitated according to a common procedure. Thereafter, the brain was taken out from each mouse and cooled by immersion in a cold Ringer's solution$^{note\ 1)}$ (at 0° C.) for 1 to 2 minutes, and then, coronal brain slices with a thickness of 400 μm were prepared using a microslicer (ZERO 1, Dosaka EM Co., Ltd.). Subsequently, the coronal brain slices were regained at room temperature for 1 hour in a chamber (acrylic incubation chamber manufactured by Harvard Corporation) in which a Ringer's solution aerated with 95% O$_2$ and 5% CO$_2$ was circulated.

(2) Enzymatic Treatment of Brain Slices

The brain slices were immersed in an enzyme solution (31° C., maintained at pH 7.4 by aeration with 95% O$_2$ and 5% CO$_2$) prepared by dissolving a proteolytic enzyme, Pronase (10 mg/60 mL) in the above-mentioned Ringer's solution, thereby performing an enzymatic treatment (the immersion time was 18 to 20 minutes in the case of the juvenile mouse brain, and 50 to 70 minutes in the case of the maturation mouse brain). Immediately after a lapse of a predetermined time period, the brain slices were immersed in 100 mL of a HEPES solution$^{note\ 2)}$ containing 10 mM glucose to stop the enzymatic reaction.

(3) Separation of Midbrain Substantia Nigra Pars Reticulata

A 60 mm plastic dish with a silicone-coated bottom was filled with a HEPES solution$^{note\ 2)}$ containing 10 mM glucose (at room temperature), and the above prepared brain slices were immersed therein. Each of the brain slices was immobilized with two 27-G injection needles, and the right and left midbrain substantia nigra pars reticulata were punched out using a 18-G injection needle having an elliptically shaped tip end under microscope, which was stored at room temperature in the above-mentioned HEPES solution$^{note\ 2)}$ (in a 35-mm culture dish).

(4) Isolation of Substantia Nigra Pars Reticulata Neurons

Neurons were isolated by trituration using a glass pipette having a tip end diameter adjusted to various diameters, and were allowed to adhere to a 35-mm glass bottom culture dish$^{note\ 4)}$ coated with poly-L-lysine$^{note\ 3)}$.

Note 1) Ringer's Solution for Isolation 124 mM NaCl, 26 mM NaHCO$_3$, 5 mM KCl, 1.24 mM KH$_2$PO$_4$, 2.4 mM CaCl$_2$, 1.3 mM MgSO$_4$.7H$_2$O, 10 mM Glucose, the solution was maintained at pH 7.4 by aeration with 95% O$_2$ and 5% CO$_2$.

Note 2) HEPES Solution 150 mM NaCl, 5 mM KCl, 1 mM MgCl$_2$, 2 mM CaCl$_2$, HEPES 10 mM, the solution was adjusted to pH 7.4 with 1 M Tris (2-amino-2-hydroxymethyl-1,3-propanediol) solution. The concentration of glucose was 10 mM at the time of preparation of the sample. A glucose-free solution was used in the 2-NBDG and 2-NBDLG solutions.

Note 3) poly-L-lysine Coating for Coverslip (for Neurons)

A solution obtained by dissolving 5 mg of poly-L-lysine hydrobromide (SIGMA P6282) in 50 mL of 0.15 M boric acid (adjusted to pH 8.4 with NaOH) was used as a stock solution and stored in a refrigerator. This stock solution was diluted to 1/1000 with 0.15 M boric acid, and the diluted solution was dropped onto the center of a coverslip (13 mm×22 mm No. 0 glass, Matsunami Glass Ind., Ltd.). The coverslip was left as such at room temperature for 20 minutes, and then washed with distilled water, followed by natural drying.

Note 4) Preparation of Glass Bottom Culture Dish

The above-mentioned glass coverslip having an upper surface coated with poly-L-lysine[note 3)] was attached to an elliptically-shaped hole (5 mm×14 mm) of a 35-mm culture dish (Matsunami code D109501) having the elliptically-shaped hole on the bottom from the back surface using a silicone grease (Dow Corning 111 Sealant) and fixed thereto so that water does not leak out.

(B) Preparation of 2-NBDG Solution and 2-NBDLG Solution (1) Preparation of Lyophilized Product 2-NBDG (or 2-NBDLG), which was purified by HPLC, and the purity of which was confirmed by NMR and HPLC, and the content of which was confirmed by an elemental analysis was weighed and dissolved in water. The solution was dispensed into vials such that each vial contained a net weight of 0.5 mg of 2-NBDG (or 2-NBDLG) and lyophilized, which was stored in dark at −20° C. or lower.

(2) Preparation of 2-NBDG (or 2-NBDLG) Solution

When the above-mentioned 2-NBDG (or 2-NBDLG) vial was used, the entire amount of one vial was dissolved in 7.3 mL of a glucose-free HEPES solution[note 2)], whereby a 2-NBDG (or 2-NBDLG) solution at a final concentration of 200 μM was prepared.

(C) Perfusion Device and Fluorescence Detection Device for 2-NBDG (or 2-NBDLG) Solution when Using Normal Fluorescence Microscope In a homemade perfusion chamber (Non-patent document 2) mounted on a heating-type xy stage (Zeiss Tempcontrol 37-2) of an inverted fluorescence microscope from Zeiss Axiovert 135 (100 W, a xenon light source), a 35-mm glass bottom culture dish[note 4)] was placed, and a glass coverslip (neurons were placed thereon according to the method described in (A)) placed in the dish was perfused with a HEPES solution for recording at a rate of 1.3 mL/min.

The introduction of the perfusion solution was performed as follows. A tube extending from a medium bottle (a stainless steel pipe and a Pharmed tube were connected to each other so that gaseous partial pressure did not change) was introduced into the 35-mm glass bottom culture dish[note 4)] using a peristaltic pump (MCP pump 12 rollers, Ismatec, Inc.). A three-way stopcock attached just upstream of the peristaltic pump was used for changing over the solution. Incidentally, the heating of the above-mentioned tube was controlled previously by the DC power supply in accordance with the perfusion rate such that the temperature of the perfusion solution in the chamber was 36 to 37° C. using a nichrome wire for adjusting the temperature in the stainless steel pipe portion upstream of the chamber.

The perfusion solution introduced into the 35-mm glass bottom culture dish[note 4)] was gently sucked using a vacuum pump subjected to pressure adjustment, and by the adjustment of the suction port, the liquid level of the solution on the cells was regulated. Further, before each experiment, the uniformity and reproducibility of the flow and the temperature of the perfusion solution were confirmed previously using a dye solution and a microthermistor probe (IT-23, Physitemp Instruments, Inc.) (Non-patent document 2).

In the fluorescence detection, a 450-490 nm standard bandpass excitation filter manufactured by Zeiss, Inc., a 510 nm dichroic mirror, and a 515-565 nm emission filter were used without using an ND filter, and as the objective lens, a Zeiss Plan Neofluar ×20 lens (NA 0.50) was used. As the condenser lens, a long working distance type was used, and the intensity of the transmitted light was adjusted using an ND filter. In the image capture, a SIT camera C2400-08 and a camera controller C2400, and an image capture software Argus 50 manufactured by Hamamatsu Photonics K.K. were used.

(D) Method for Administering 2-NBDG Solution and 2-NBDLG Solution and Protocol for Capturing Images (1) Method for Administering 2-NBDG Solution and Protocol for Capturing Images An image (512×483, 16 bit) was captured with the shutter of the SIT camera closed, and the background noise pattern specific to the SIT camera was obtained (the drawing is omitted).

Subsequently, the shutter of the light path to the SIT camera was opened, and a phase contrast image and an autofluorescence image of cells before administering 2-NBDG were captured.

The three-way stopcock upstream of the peristaltic pump was tilted down toward the side of the 2-NBDG solution so as to administer the 200 μM 2-NBDG solution for 1 minute to incorporate 2-NBDG, and soon thereafter, the solution was returned to the HEPES solution which did not contain 2-NBDG, and fluorescence images were captured at 10 minutes and 30 minutes after initiation of washing. Incidentally, it was confirmed that the cell morphology did not change during this 30 minutes by capturing a phase contrast image after 30 minutes.

As the method for processing the fluorescence image data, the following method was adopted.

(a) Background Subtraction

When fluorescence images captured with the shutter of the light path to the SIT camera opened were displayed, they were displayed as images obtained by subtracting the background noise pattern captured with the shutter closed.

(b) Shading Correction

A fluorescence image obtained by applying the 200 μM 2-NBDG solution to a cell-free dish and capturing it under the same image capturing condition as in the experiment was used as a standard image for shading correction. This image shows a manner of two-dimensional distribution of obtained fluorescence intensity derived from the light source unevenness and the property of an optical system including a lens and a camera. In order to prevent the result of administration of 2-NBDG to cells from being affected by the above-mentioned optical unevenness and the like, the shading correction algorithm of Argus 50[note 5)] was applied to the respective fluorescence images and the above-mentioned standard images for shading correction, and the fluorescence images after correction were stored as fluorescence images corrected for shading.

(c) Correction for Degree of Washing Due to Difference in Location in Dish

The size of the coverslip portion (5 mm×14 mm) of the dish is about 1000 times larger than that of a cell, and depending on the location in the dish where the cell to be observed is present, a slight difference occurs in the time period for perfusion with the 2-NBDG solution and washing. Therefore, in order to reduce the effect of the regional difference in perfusion on the evaluation for the degree of incorporation of 2-NBDG into cells, the following correction was performed. That is, substantially in the center of the viewed screen of the SIT camera (x,y)=(256, 242), a 30×30 pixel area was set, and the average fluorescence intensity $B_0$ of this area was detected for each captured fluorescence image. Incidentally, the position of the xy stage was adjusted in advance at the time of capturing an image so that the cell was not present in the center of the screen. Subsequently, a value $(B(x,y)/B_0)$ obtained by dividing the fluorescence intensity $B(x,y)$ at each point by this $B_0$ was defined as a fluorescence intensity at each point (x,y).

(d) Gamma Enhancement of Fluorescence Intensity

Images were obtained by 32-times integration (duration: 1 sec). Further, the fluorescence images obtained by application of 2-NBDG were obtained by reducing the excitation intensity of the light source for minimizing the color fading, and therefore, in order to easily clarify the difference in intensity depending on the location, the intensity was adjusted (gamma 0.3), and for the purpose of image processing, the 16 bit images were reduced to 8 bit and displayed.

Note 5) Shading Correction Algorithm of Argus 50

$$C(x,y)=A(x,y)\times[B\max/B(x,y)]$$

C(x,y)=Image after correction
A(x,y)=Image before correction
B(x,y)=Shading standard image
Bmax=Maximum brightness among B(x,y)

As A and B, images after subtracting the background noise are used.

(2) Method for Administering 2-NBDLG Solution and Protocol for Capturing Images

Exactly the same method for administering 2-NBDG solution and protocol for capturing images were used.

(Result of Application)

Figure 2:
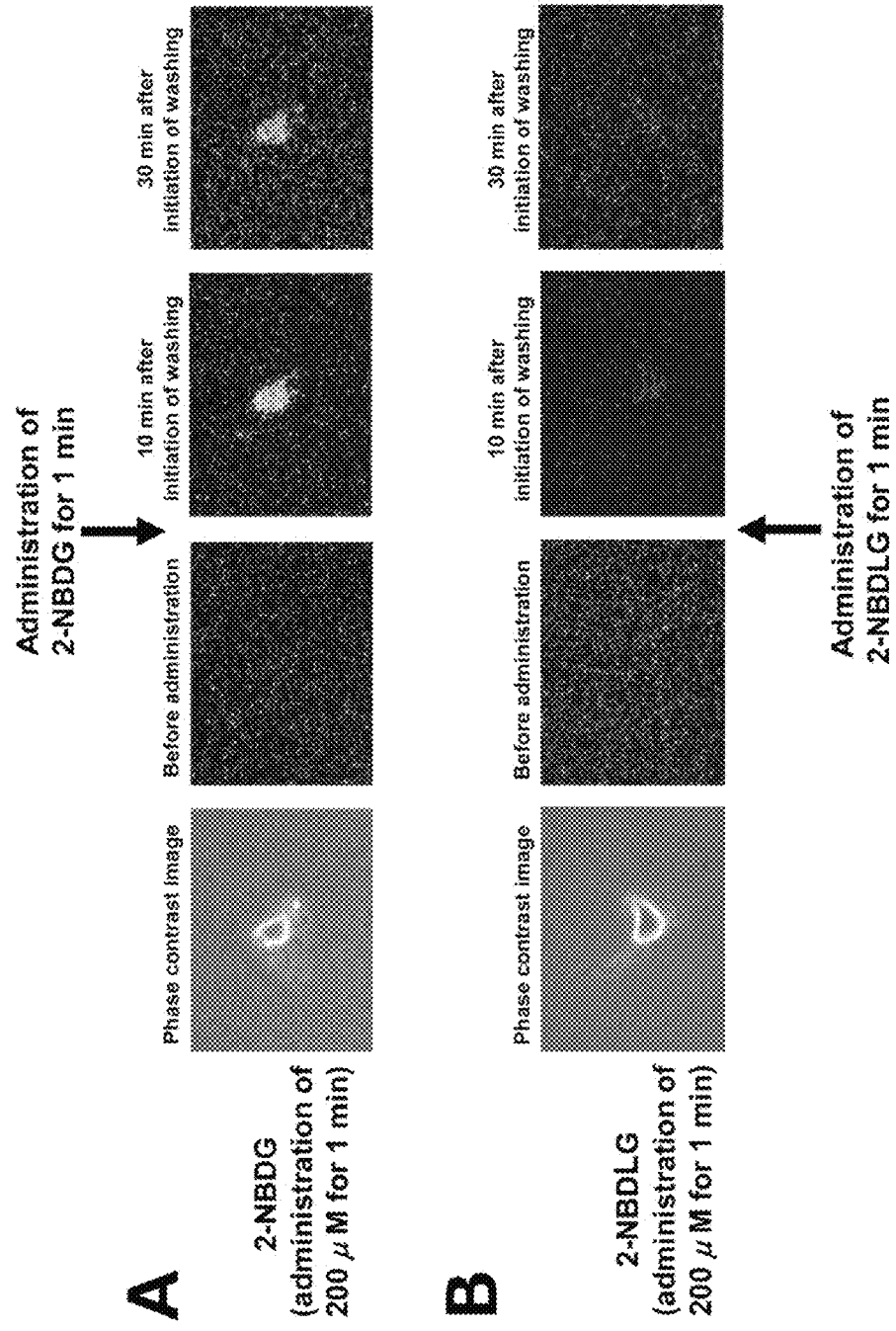
[FIG. 2] Images captured by a normal fluorescence microscope when 2-NBDG or 2-NBDLG was administered to acutely isolated neurons in Example 1.

The result is shown in FIG. 2. As is apparent from FIG. 2, in this experiment, by the administration of 2-NBDG, green fluorescence from the cell was observed, however, by the administration of 2-NBDLG, almost no green fluorescence from the cell was observed. Accordingly, it could be evaluated that this difference was based on the specific incorporation of 2-NBDG into the cell. Incidentally, in the experiment, the cells to which 2-NBDG was administered and the cells to which 2-NBDLG was administered were subjected to patch clamp analysis to examine the action potentials of the respective cells, and it was confirmed that the action potentials of the respective cells were equivalent to each other, whereby a possibility that the difference in the activities of the cells may affect the fluorescence intensities was eliminated, and the validity of the evaluation could be verified. From the above result, it was found that by administering 2-NBDLG as the control for 2-NBDG, the specific incorporation of D-glucose into cells can be accurately evaluated.

Example 2

Example of Applying 2-NBDG and 2-TRLG to Neurons 2-1: Synthesis of 2-NBDG

The synthesis of 2-NBDG was performed according to the method described in Non-patent document 1.

2-2: Synthesis of 2-TRLG

[Chemical 5]

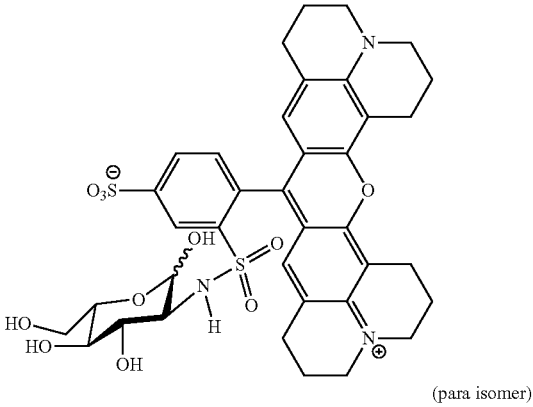
(ortho isomer)

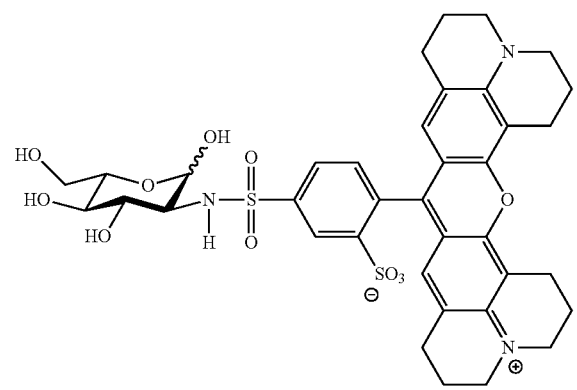
(para isomer)

In a brown flask, L-glucosamine hydrochloride (51.9 mg) was placed and dissolved in water (300 µl), and then, dehydrated DMF (1.70 ml) was added thereto. Under an argon atmosphere, diisopropylethylamine (84.1 µl) was added thereto, and further a solution in which sulforhodamine 101 chloride (30.0 mg) was dissolved in dehydrated DMF (1.50 ml) was added thereto, and the resulting mixture was stirred at room temperature. After 35 minutes, 50% acetic acid (6.00 ml) was added thereto, followed by purification by HPLC. A target fraction was collected and lyophilized. Incidentally, since sulforhodamine 101 chloride which is a fluorescent reagent is a mixture of two isomers (ortho and para isomers), the product was also a mixture of two isomers (ortho and para isomers), and therefore, a compound whose retention time in HPLC is short (high-polar 2-TRLG) and a compound whose retention time in HPLC is long (low-polar 2-TRLG) were separated and purified.

Yield of high-polar 2-TRLG: 10.3 mg
Yield of low-polar 2-TRLG: 6.0 mg
Overall yield: 16.3 mg
Overall yield ratio: 44%

(High-polar 2-TRLG)

$^1$H-NMR spectrum (400 MHz, $CD_3OD$, δ, ppm): 8.57 [d, 0.7H, J=1.7 Hz, H3' of Ph (α-form)], 8.49 [d, 0.3H, J=1.7 Hz, H3' of Ph (δ-form)], 8.02 [dd, 0.7H, J=1.7 Hz and 8.0 Hz, H5' of Ph (α-form)], 7.98 [dd, 0.3H, J=1.7 Hz and 8.0 Hz, H5' of Ph (β-form)], 7.24 [d, 0.7H, J=8.0 Hz, H6' of Ph (α-form)], 7.19 [d, 0.3H, J=8.0 Hz, H6' of Ph (β-form)], 6.84 and 6.68 [s×2, 0.3H×2, H8" and H10" (β-form)], 6.73 and 6.55 [s×2, 0.7H×2, H8" and H10" (α-form)], 4.35 [d, 0.3H, J=8.5 Hz, H1 (β-form)], 2.60-3.72 [m, 21H, H3, H4, H5, H6a, and H6b, H1", H3", H5", H7", H11", H13", H15" and H17" (α-form and β-form)], 2.01 and 1.86 [m, 8H, H2", H6", H12" and H16" (α-form and β-form)]

ESI-MS: calcd for $C_{37}H_{42}N_3O_{11}S_2$ [M+H]$^+$768.2, found 768.2

(Low-polar 2-TRLG)

$^1$H-NMR spectrum (400 MHz, CD$_3$OD, δ, ppm): 8.58 [d, 0.75H, J=1.8 Hz, H3' of Ph (α-form)], 8.54 [d, 0.25H, J=1.8 Hz, H3' of Ph (β-form)], 8.02 [dd, 0.75H, J=1.8 Hz and 8.0 Hz, H5' of Ph (α-form)], 7.98 [dd, 0.25H, J=1.8 Hz and 8.0 Hz, H5' of Ph (β-form)], 7.27 [d, 0.75H, J=8.0 Hz, H6' of Ph (α-form)], 7.23 [d, 0.25H, J=8.0 Hz, H6' of Ph (β-form)], 6.56 and 6.54 [br.s×2, 2H, H8" and H10" (α-form and β-form)], 4.90 [d, 0.75H, J=3.4 Hz, H1 (α-form)], 4.42 [d, 0.25H, J=8.3 Hz, H1 (β-form)], 2.60-3.70 [m, 21H, H3, H4, H5, H6a, H6b, H1", H3", H5", H7", H11", H13", H15" and H17" (α-form and β-form)], 2.00 and 1.85 [m, 8H, H2", H6", H12" and H16" (α-form and β-form)]

ESI-MS: calcd for $C_{37}H_{42}N_3O_{11}S_2$ [M+H]$^+$768.2, found 768.2

2-3: Application of 2-NBDG and 2-TRLG to Acutely Isolated Neurons (Capture of Images by Real-Time Laser Scanning Confocal Fluorescence Microscope)

(A) Preparation of Acutely Isolated Neurons

The preparation of acutely isolated neurons was performed in the same manner as in Example 1.

(B) Preparation of Mixed Solution of 2-TRLG and 2-NBDG

Since 2-TRLG is insoluble in water, first, 1.54 mg of TRLG was dissolved in a solution of 30% acetonitrile and 70% H$_2$O, whereby a 2 mM 2-TRLG solution was prepared. Then, 10 μL of this 2 mM solution was dissolved in 1 mL of a glucose-free HEPES buffer solution$^{note\ 6)}$ containing 100 μM 2-NBDG so as to dilute the 2 mM solution to 100-fold, whereby a mixed solution of 20 μM 2-TRLG and 100 μM 2-NBDG was obtained.

Note 6) Preparation of Glucose-Free Hepes Buffer Solution Containing 100 μM 2-NBDG The glucose-free HEPES buffer solution containing 100 μM 2-NBDG was prepared by adding 14.6 mL of a glucose-free HEPES solution$^{note\ 2)}$ to 0.5 mg of a 2-NBDG vial prepared according to the method described in Example 1, 1-3, (B), (1).

(C) Method for Administering Mixed Solution of 2-TRLG and 2-NBDG and Protocol for Capturing Images in the Case of Using Real-Time Laser Scanning Confocal Microscope (1) Method for Administering Mixed Solution of 20 μM 2-TRLG and 100 μM 2-NBDG (a) Preparation of Micropipette A commercially available 1-mm glass capillary tube (B100-75-15, Sutter Instrument) was pulled by a puller (P-97, Sutter Instrument), whereby two glass pipettes having one end closed were prepared. Then, by using a microforge (MF-90, manufactured by Narishige Co., Ltd.), a small glass ball attached to the tip end of the platinum heater of the microforge was heated to such an extent that the color of the glass ball does not turn red and instantaneously brought into contact with the tip end of the glass pipette, and simultaneously with the contact, the heater was switched off, whereby a micropipette having an open tip end with an outer diameter of from 3 to 4 μm (an inner diameter of from 1.5 to 3 μm) was obtained.

(b) Filling of Mixed Solution of 2-TRLG and 2-NBDG

100 μL of the mixed solution of 20 μM 2-TRLG and 100 μM 2-NBDG prepared in (B) was poured into a cap of a microtube, and a thin tygon tube was connected to the back end of the micropipette prepared in (a), and then, a 10-cc syringe was connected thereto via a three-way stopcock. Thereafter, the tip end of the micropipette was immersed in the above mixed solution using a micromanipulator and the syringe was rapidly pulled, whereby the mixed solution was filled in the tip end of the micropipette. Subsequently, the mixed solution was filled in the micropipette from the back end thereof using a fine syringe needle (MicroFil, manufactured by WPI, Inc.).

(c) Connection of Micropipette to Microinjector

The micropipette filled with the mixed solution was connected to a universal holder of a commercially available microinjector (Transjector 5246, manufactured by Eppendorf Co., Ltd.). Then, the universal holder was connected to a micromanipulator (a three-dimensional joystick hydraulic manipulator, Narishige Co., Ltd.) on a confocal microscope stage. A cell-free dish was prepared, and the micropipette was immersed in a HEPES solution$^{note\ 2)}$ and then, the ejection of a dye solution from the tip end of the micropipette was confirmed by fluorescence while applying a positive pressure (1500 hPa) in an injection mode. Subsequently, a correction pressure was applied to the micropipette by utilizing the automatic pressure regulating function of the microinjector, and thereby a state in which leakage of the mixed solution from the tip end of the micropipette or suction of an external solution into the tip end thereof was not caused was maintained.

(d) Approach of Glass Pipette to the Vicinity of Cell 3 mL of a HEPES solution$^{note\ 2)}$ was added to a 35-mm glass bottom culture dish$^{note\ 4)}$ having a glass bottom to which neurons were adhered, and further 3 mL of mineral oil (M8410, Sigma CO., Ltd.) was laminated thereon. Subsequently, this glass bottom culture dish was fixed to the universal frame (Leica 11600234) on the confocal microscope stage, and the micropipette was brought closer to the vicinity of the cell (such that the distance between the tip end of the pipette and the center of the cell became 80 μm) so as to allow the micropipette to come within the visual field of a ×63 lens (Zoom 1.7) by operating the micromanipulator while making an observation in a live mode, and fixed to an xyz position where the fluorescent solution ejected from the pipette uniformly covered the entire cell.

(2) Detailed Condition for Capturing Images

A real-time laser scanning confocal microscope, TCS SP5 manufactured by Leica, Inc. (the main body was DMI 6000 CS trino) was used in a high-speed (8000 Hz) resonant scanning mode.

As the laser source, a 488 nm argon laser was used at 15% power. As the lens, a ×63 oil lens (HCX PL APO Lambda Blue, NA 1.40) was used, and a 500 nm dichroic mirror (RSP 500) was used.

A total of three detectors (channels): a photomultiplier detector for light in a green wavelength range (PMT1) and a photomultiplier detector for light in a red wavelength range (PMT2), and also a detector for transmitted light (PMTTrans) were used simultaneously, and 512×512 pixel images were captured. The detection sensitivity was set as follows: PMT1: 868 V, PMT2: 868 V, and PMTtrans: 245 V. Incidentally, the optimal values of the detection wavelength ranges of green fluorescence (500-580 nm) and red fluorescence (580-740 nm) were selected not on the basis of an emission filter system, but on the basis of a system using a prism spectroscope and a slit in combination (standard of TCS SP5, Leica, Inc.).

Green, red, and transmitted light laser scanning were performed simultaneously. In the case where transmitted light images are captured, if a differential interference contrast (DIC) technique is used, a time to switch over for disposing a polarizer and an analyzer in a light path is required, and therefore, at the time of performing this scanning, simple bright-field images were captured.

The optical zoom was set to a 1.7-fold optical zoom which is the lowest value in the resonant mode, and the pinhole size was set to 6.28 which is the highest value in the case of using a ×63 lens. It was confirmed in the captured images that even in the case of this pinhole size, the nucleus and the cytoplasm in the cell could be practically distinguished from each other in the z-axis direction. By performing three scanning, an average image was captured.

(3) Method for Administering the Mixed Solution of 2-TRLG and 2-NBDG

The administration was performed in a room maintained at a constant room temperature (24° C.) for 24 hours.

(a) Capture of Images Before Administration

Immediately before the mixed solution was administered, images of fluorescence in the respective green and red wavelength ranges, and transmitted light images were captured by the method described in the above (2).

(b) Administration of Mixed Solution

The mixed solution of 20 μM 2-TRLG and 100 μM 2-NBDG was administered for 1 minute (administration amount: 0.6 μL) using an ejection pressure of 1500 hPa such that the solution completely covered the entire neurons. Whether the administered solution covered the entire cells was confirmed every time without fail by capturing images of fluorescence in the respective green and red wavelength ranges, and transmitted light images during the administration. When the ejection of the mixed solution was stopped, the mixed solution was immediately diffused in the entire HEPES solution (3 mL) and diluted to 5000-fold, and therefore, the background fluorescence reached a negligible level after 1 minute. Further, it was considered that the amount incorporated into cells was a sufficiently lower level than the detection limit of the device within an experimental time (at most 1 hour).

(c) Capture of Images after Administration

After the administration of the mixed solution was stopped, images of fluorescence in the respective green and red wavelength ranges, and transmitted light images were captured by the method described in the above (2) every 5 minutes.

(Result of Application)

Figure 3:
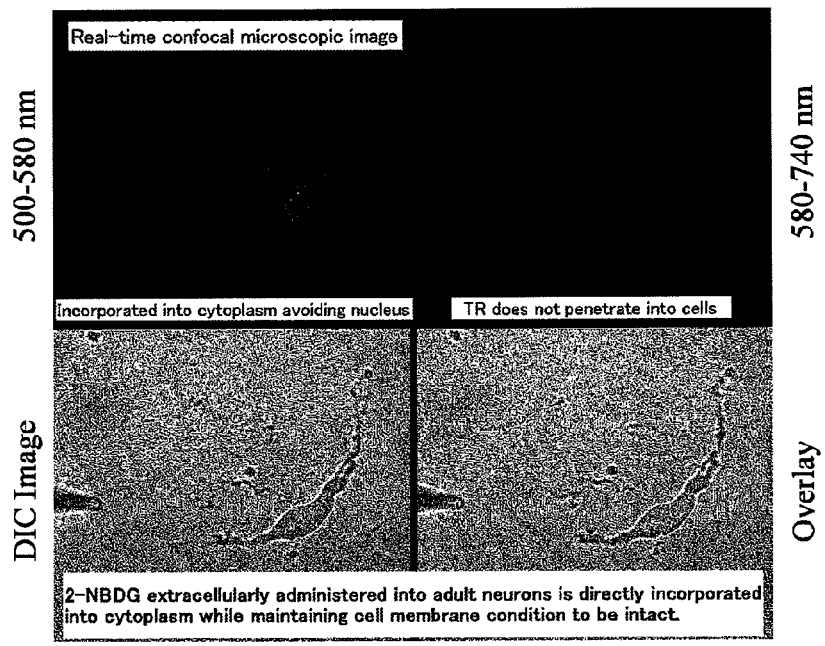
[FIG. 3] Images captured by a real-time laser scanning confocal fluorescence microscope when 2-NBDG and 2-TRLG were administered simultaneously to acutely isolated neurons in Example 2.
Figure 4:
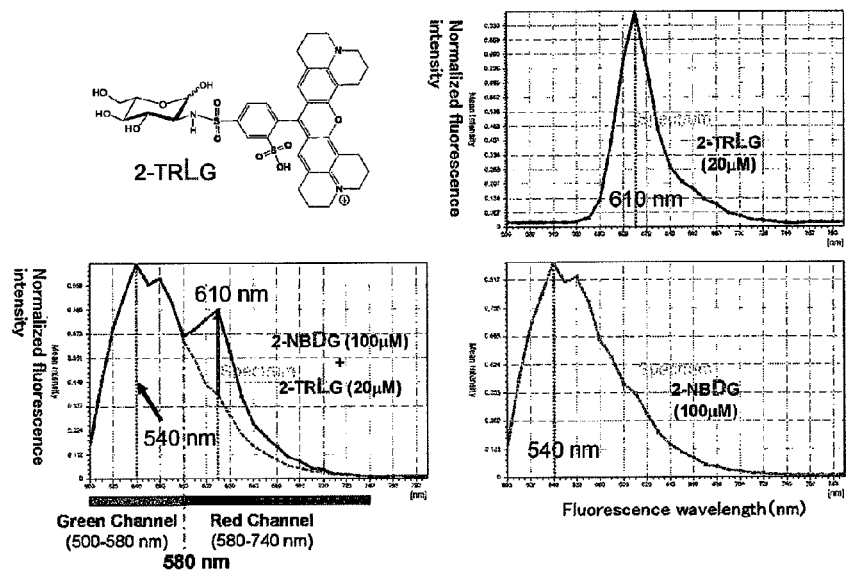
[FIG. 4] Fluorescence spectrum chart of a mixed solution of 2-TRLG and 2-NBDG in Example 2.

FIG. 3 shows a fluorescence image and a transmitted light image captured at 1 minute after stopping the administration. As is apparent from FIG. 3, in this experiment, yellow to red fluorescence based on the incorporation of 2-TRLG into the cell was not observed, and only green fluorescence derived from 2-NBDG was observed, and therefore, it could be evaluated that in this cell, a part of the cell membrane was not disrupted and the membrane was not in a state where both 2-NBDG and 2-TRLG were nonspecifically incorporated, and 2-NBDG was specifically incorporated into the cell (for example, when a hemichannel of the cell membrane is open, it allows a molecule having a molecular weight of about 1000 or less to pass through the cell membrane, and therefore, 2-TRLG having a molecular weight of 768 is also incorporated, however, the fact that the incorporation of 2-TRLG is not observed means that the incorporation of a molecule through the hemichannel is not caused). Incidentally, the validity of this evaluation result is supported by the result that when the mixed solution of 20 μM 2-TRLG and 100 μM 2-NBDG is used, green fluorescence emitted by 2-NBDG can be detected by detecting fluorescence at around 540 nm, and red fluorescence emitted by 2-TRLG can be detected by detecting fluorescence at around 610 nm (in the case of pH 7.4, the maximum fluorescence wavelength of 2-NBDG is 540 nm, and the maximum fluorescence wavelength of 2-TRLG is 610 nm, see FIG. 4). Further, by using a confocal microscope, an intracellular region and an extracellular region can be distinguished, and therefore, the confocal microscope is an effective device in the present invention.

Example 3

Synthesis of 2-DBDLG

[Chemical 6]

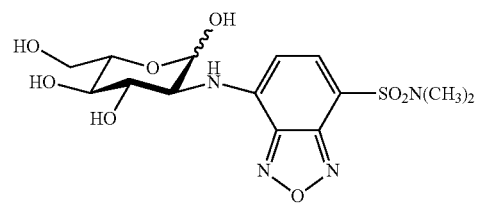

In a brown flask, 4-(N,N-dimethylaminosulfonyl)-7-fluoro-2,1,3-benzoxadiazole (DBD-F) (100 mg) was placed and dissolved in a mixed solvent of methanol (2.00 ml) and THF (2.00 ml). Under an argon atmosphere, a solution in which L-glucosamine hydrochloride (49.8 mg) was dissolved in 0.3 M NaHCO$_3$ solution (1.08 ml) was added thereto, and the resulting mixture was stirred at room temperature. After 48 hours, methanol was removed by concentration under reduced pressure, and the resulting precipitates (unnecessary substances derived from DBD-F) were removed by filtration. The precipitates were washed with water, and the filtrate and the washing solution were combined, followed by purification by HPLC. A target fraction was collected and lyophilized, whereby a target product was obtained (yield: 35.8 mg, yield ratio: 38%).

$^1$H-NMR spectrum (400 MHz, D$_2$O, δ, ppm): 7.82 and 7.84 (d×2, 0.5H×2, J=8.3 Hz and 8.3 Hz, H-6'), 6.42 and 6.46 (d×2, 0.5H×2, J=8.3 Hz and 8.3 Hz, H-5'), 5.31 [br.d, 0.5H, J=2.7 Hz, H-1 (α-form)], 4.79 [br.d, 0.5H, J=8.3 Hz, H-1 (β-form)], 3.43-3.90 [m, 6H, H-2, H-3, H-4, H-5, H-6a, and H-6b (α-form and β-form)], 2.65 (s, 6H, Me$_2$NSO$_2$—)

ESI-MS: calcd for C$_{14}$H$_{21}$N$_4$O$_8$S [M+H]$^+$405.1, found 405.1

Example 4

Application to Evaluation for the State of *Escherichia coli*

Figure 5:
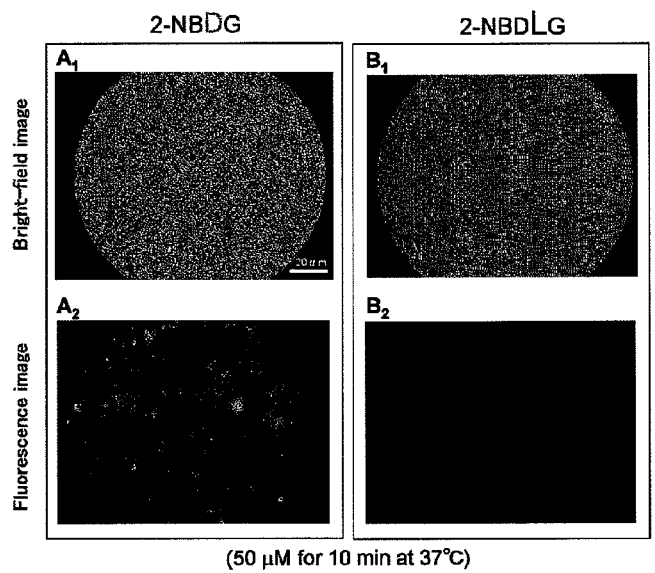
[FIG. 5] Result obtained by applying 2-NBDG or 2-NBDLG to the evaluation for the state of *Escherichia coli* in Example 4.

*Escherichia coli* K12 was cultured with shaking overnight at 37° C. A 1 mL portion of the culture was centrifuged to collect cells, and the cells were suspended in 1 mL of phosphate buffered saline (PBS, a mixed solution of 0.01 M phosphate buffer and 0.137 M NaCl at pH 7.4). A 90 μL portion of the suspension was taken out, and 10 μL of the 2-NBDG solution or the 2-NBDLG solution was added thereto to give a final concentration of 50 μM, and then, an incorporation reaction was allowed to proceed at 37° C. for 10 minutes. After the reaction, the cells were collected by centrifugation and resuspended in PBS, and the cells were microscopically observed (objective lens ×10) and recorded using a CCD camera for microscopic observation. The result is shown in FIG. 5. As is apparent from FIG. 5, significant fluorescence due to the incorporation of 2-NBDG into the cells could be detected, however, fluorescence due to the incorporation of 2-NBDLG into the cells could not be detected under the same measurement condition as that for 2-NBDG. Incidentally, the same experiment was performed for dead cells prepared by treating the live cells with 70% ethanol at room temperature for 10 minutes, and as a result, a difference in the result of the fluorescence detection for 2-NBDG and 2-NBDLG was not observed (from another experiment).

Example 5

Synthesis of 2-NMAG

[Chemical 7]

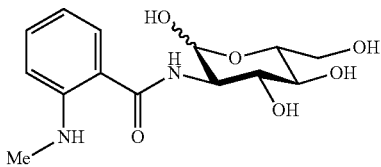

In a brown flask, D-glucosamine hydrochloride (215 mg) was placed and dissolved in water (1.0 ml), and DMF (9.0 ml) was added thereto. Under an argon atmosphere, N-methylanthranilic acid (another name: 2-(methylamino)benzenecarboxylic acid) (151 mg) and 1-hydroxybenzenetriazole (135 mg) were added thereto, and the resulting mixture was cooled in ice. Further, 1-ethyl-3-(3-dimethylaminopropyl)-carbodiimide (187 µl) was added thereto, and the resulting mixture was stirred at 0° C. After 2 hours, the mixture was concentrated under reduced pressure, and water was added to the obtained residue and the mixture was lyophilized. Water was added to the lyophilized product, and unnecessary substances which were derived from the reagents and insoluble in water were removed by filtration, and the unnecessary substances were washed with water. The filtrate and the washing solution were combined, followed by purification by HPLC. A target fraction was collected and lyophilized, whereby a target product was obtained (yield: 140 mg, yield ratio: 45%).

$^1$H-NMR spectrum (400 MHz, $D_2O$, δ, ppm): 7.44 (m, 2H, Ar), 6.86 (d, 1H, J=8.2 Hz, Ar), 6.78 (dd, 1H, J=7.5 and 7.5 Hz, Ar), 5.29 (d, 0.5H, J=3.7 Hz, H-1α), 4.80 (d, 0.5H, J=8.3 Hz, H-1β), 3.48-4.05 (m, 6H, H-2, H-3, H-4, H-5, H-6, H-6), 2.78 (s, 3H, Me)

ESI-MS: calcd for $C_{14}H_{21}N_4O_8S$ [M+H]$^+$313.1, found 313.1

Example 6

Synthesis of 2-NMALG

2-NMALG can be synthesized in the same manner as the method for synthesizing 2-NMAG except that L-glucosamine hydrochloride is used in place of D-glucosamine hydrochloride.

Example 7

Usefulness in the Case of Using 2-NBDG, 2-TRLG, and 2-NMALG by Mixing them

Figure 6:
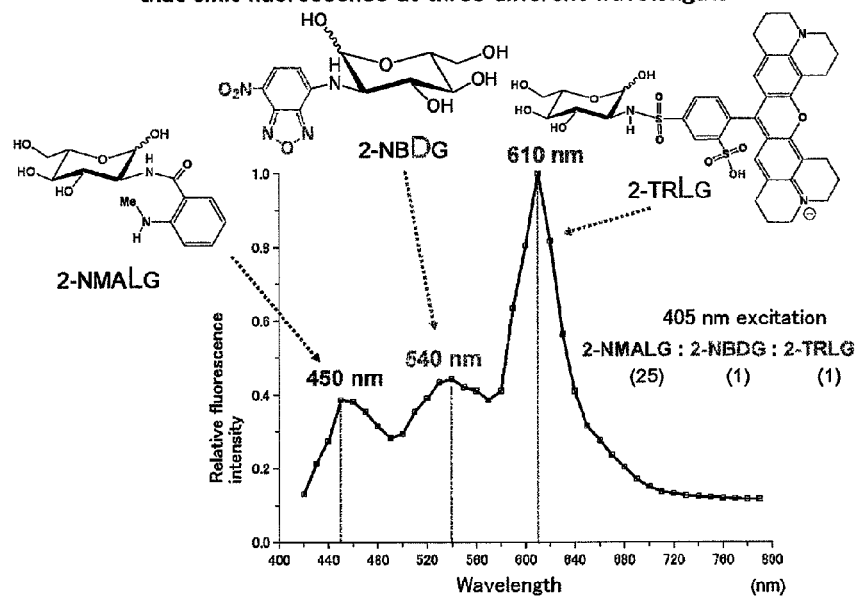
[FIG. 6] Fluorescence spectrum chart of a mixed solution of 2-NBDG, 2-TRLG, and 2-NMALG in Example 7.

A fluorescence spectrum chart in the case where a solution obtained by mixing 2-NBDG as the D-glucose derivative that has a fluorescent chromophore in the molecule and is specifically incorporated into cells, and 2-TRLG and 2-NMALG as the L-glucose derivative that has a fluorescent chromophore in the molecule at 1:1:25 (molar ratio) was excited by laser light at 405 nm is shown in FIG. 6. As is apparent from FIG. 6, by this combination, the blue fluorescence emitted by 2-NMALG at around 450 nm which is the maximum fluorescence wavelength of 2-NMALG, the green fluorescence emitted by 2-NBDG at around 540 nm which is the maximum fluorescence wavelength of 2-NBDG, and the red fluorescence emitted by 2-TRLG at around 610 nm which is the maximum fluorescence wavelength of 2-TRLG can be detected, respectively. Since 2-TRLG and 2-NMALG are each an L-glucose derivative, they will be incorporated into cells only nonspecifically. However, the sizes (bulkiness) of the fluorescent chromophores of both glucose derivatives are different, and therefore, for example, in the case where the degree of the deterioration state of the cell membrane is small, only 2-NMALG having a small fluorescent chromophore is incorporated into cells, and 2-TRLG having a large fluorescent chromophore is not incorporated into cells until the degree of the deterioration state of the cell membrane becomes large. Accordingly, a difference in the nonspecifically incorporated L-glucose derivative based on a difference in the degree of the deterioration state of the cell membrane can be detected, and therefore, the specific incorporation of D-glucose into cells relative to L-glucose can be evaluated and also the degree of the deterioration state of the cell membrane can be evaluated by the method.

Industrial Applicability

The present invention has an industrial applicability in the point that it can provide a method for accurately evaluating the specific incorporation of D-glucose into cells.

The invention claimed is:
1. A method for evaluating the specific incorporation of D-glucose into cells relative to L-glucose, characterized by comprising contacting a D-glucose derivative that has a fluorescent chromophore in the molecule and an L-glucose derivative that has a fluorescent chromophore in the molecule with different cells in the same cell strain to be evaluated, respectively, comparing the fluorescence emitted by the D-glucose derivative with the fluorescence emitted by the L-glucose derivative, and evaluating the specific incorporation of D-glucose into cells relative to L-glucose by taking the difference between the two kinds of fluorescence intensities wherein the D-glucose derivative is incorporated into cells with being mediated by a glucose transporter.

2. The method according to claim 1, characterized in that as the D-glucose derivative that has a fluorescent chromophore in the molecule, a D-glucose derivative that has an N-(7-nitrobenz-2-oxa-1,3-diazol-4-yl) amino group in the molecule is used.

3. The method according to claim 2, characterized in that as the D-glucose derivative that has an N-(7-nitrobenz-2-oxa-1,3-diazol-4-yl)amino group in the molecule, D-deoxyglucose having an N-(7-nitrobenz-2-oxa-1,3-diazol-4-yl)amino group attached to the 2-position thereof is used.

4. The method according to claim 2, characterized in that as the L-glucose derivative that has a fluorescent chromophore in the molecule, an L-glucose derivative that has an N-(7-nitrobenz-2-oxa-1,3-diazol-4-yl)amino group in the molecule is used.

5. The method according to claim 4, characterized in that as the L-glucose derivative that has an N-(7-nitrobenz-2-oxa-1, 3-diazol-4-yl)amino group in the molecule, L-deoxyglucose having an N-(7-nitrobenz-2-oxa-1,3-diazol-4-yl)amino group attached to the 2-position thereof is used.

6. The method according to claim 1, characterized in that the L-glucose derivative has the fluorescent chromophore attached to the 2-position of its L-glucose moiety.

7. A method for evaluating the specific incorporation of D-glucose into cells relative to L-glucose, characterized by comprising contacting a mixture of a D-glucose derivative that has a fluorescent chromophore in the molecule and one or more L-glucose derivatives that each have, in the molecule, a fluorescent chromophore that emits fluorescence at a wavelength different from that of the fluorescence emitted by the D-glucose derivative with cells to be evaluated, and detecting the fluorescence emitted by the D-glucose derivative and the fluorescence emitted by the L-glucose derivative, respectively, wherein the D-glucose derivative is incorporated into cells with being mediated by a glucose transporter.

8. The method according to claim 7, characterized in that a difference in the maximum fluorescence wavelength is set to at least 20 nm.

9. The method according to claim 7, characterized in that as the D-glucose derivative that has a fluorescent chromophore in the molecule, a D-glucose derivative that has an N-(7-nitrobenz-2-oxa-1,3-diazol-4-yl)amino group in the molecule is used.

10. The method according to claim 9, characterized in that as the D-glucose derivative that has an N-(7-nitrobenz-2-oxa-1,3-diazol-4-yl)amino group in the molecule, D-deoxyglucose having an N-(7-nitrobenz-2-oxa-1,3-diazol-4-yl)amino group attached to the 2-position thereof is used.

11. The method according to claim 9, characterized in that as the L-glucose derivative that has, in the molecule, a fluorescent chromophore that emits fluorescence at a wavelength different from that of the fluorescence emitted by the D-glucose derivative that has a fluorescent chromophore in the molecule, an L-glucose derivative having sulforhodamine attached thereto is used, wherein the D-glucose derivative is incorporated into cells with being mediated by a glucose transporter.

12. The method according to claim 7, wherein:

said mixture comprises two or more L-glucose derivatives, each of which has a different fluorescent chromophore in the molecule.

\* \* \* \* \*